United States Patent
Xu et al.

(10) Patent No.: US 9,504,741 B2
(45) Date of Patent: Nov. 29, 2016

(54) IMMUNE METHODS AGAINST INFLUENZA VIRUSES AND COMBINATORIAL VACCINES THEREOF

(75) Inventors: Jianqing Xu, Suzhou (CN); Yang Huang, Suzhou (CN)

(73) Assignee: Vacdiagn Biotechnology Co., Ltd., Suzhou (CN)

( * ) Notice: Subject to any disclaimer, the term of this patent is extended or adjusted under 35 U.S.C. 154(b) by 48 days.

(21) Appl. No.: 14/352,961

(22) PCT Filed: Nov. 23, 2011

(86) PCT No.: PCT/CN2011/001950
§ 371 (c)(1),
(2), (4) Date: Apr. 18, 2014

(87) PCT Pub. No.: WO2013/075266
PCT Pub. Date: May 30, 2013

(65) Prior Publication Data
US 2014/0286993 A1 Sep. 25, 2014

(51) Int. Cl.
*A61K 39/145* (2006.01)
*A61K 39/12* (2006.01)
*A61K 39/00* (2006.01)

(52) U.S. Cl.
CPC ............ *A61K 39/145* (2013.01); *A61K 39/12* (2013.01); *A61K 2039/53* (2013.01); *A61K 2039/545* (2013.01); *A61K 2039/70* (2013.01); *C12N 2710/24143* (2013.01); *C12N 2760/16134* (2013.01); *C12N 2760/16234* (2013.01)

(58) Field of Classification Search
None
See application file for complete search history.

(56) References Cited

FOREIGN PATENT DOCUMENTS

| WO | 2009068992 A1 | 6/2009 | | |
|----|----|----|----|----|
| WO | 2010092476 A1 | 8/2010 | | |
| WO | 2010115133 A2 | 10/2010 | | |
| WO | WO2010/125461 A1 * | 10/2010 | ........... | A61K 39/145 |
| WO | 2010125461 A1 | 11/2010 | | |

OTHER PUBLICATIONS

Garten et al., (GenBank, No. ACP41934).*
Zhang et al. (Acta Biochimica Polonica, 2007, vol. 54, p. 307-313).*
Desbat et a., (Langmuir, Nov. 15, 2011, p. 13675-13683).*
International Search Report mailed Aug. 30, 2012, issued in corresponding International Application No. PCT/CN2011/001950, filed Nov. 23, 2011, 7 pages.

* cited by examiner

*Primary Examiner* — Agnieszka Boesen
(74) *Attorney, Agent, or Firm* — Christensen O'Connor Johnson Kindness PLLC

(57) ABSTRACT

The invention provides a method of preventing the spreading of influenza viruses, and the factors making up the said method, and especially provides one type of combinatorial vaccine and the immunization method thereof. Two of more influenza vaccines are inoculated by a certain sequence, and each influenza vaccine vaccines is inoculated at least once, and the inoculation take place two or more times; wherein each influenza vaccine includes one or more antigens, the immunogenic fragments thereof, or the coding genes thereof, and further includes a different antigen, the immunogenic fragments or the coding gene of the different antigen.

14 Claims, No Drawings

IMMUNE METHODS AGAINST INFLUENZA VIRUSES AND COMBINATORIAL VACCINES THEREOF

TECHNICAL FIELD

The invention relates to a method of preventing the spreading of influenza viruses, and the factors making up the said method, and especially relates to a combinatorial vaccine and the immunization method thereof. The principle thought of influenza combinatorial vaccine is to use different influenza hemagglutinin proteins or the coding genes thereof to carry out a sequential immunization, which means in the multiple vaccine immunization steps, different influenza hemagglutinin proteins or different coding genes thereof are employed, so as to obtain neutralizing antibodies with a high titer and a broad spectrum resistance against a number of influenza viruses. The influenza combinatorial vaccine involved in this invention may be used to prevent influenza virus infection caused by a number of subtypes.

BACKGROUND OF THE INVENTION

Influenza (called "flu" for short below) is an acute respiratory disease caused by influenza virus (called "flu virus" for short below). It spreads through the respiratory, has relative high infection rates and several of them may cause severe morbidity and mortality. The spreading of influenza virus may be divided into several classes blow according with the characters thereof.

1. Seasonal influenza. Seasonal influenza is the most common form of influenza which breaks out annually, and in autumn or winter the outbreak is often in large scale. As estimated by the World Health Organization (WHO), every year about 600 million people are infected, and 3-5 million suffer from severe conditions and result in 250-500 thousand cases of deaths. In developed countries with abundant medical resource most cases of death occur in the aged population. In the United States it is estimated that every year around 36,000 people die of seasonal influenza, and about 90% are aged above 65 (Thompson et al. Am J Public Health. 2009). Currently the marketed vaccines against seasonal influenza include inactivated virus vaccines and split vaccine for intramuscular injection, and live attenuated vaccines for mucosal vaccination, which all compose of three different types of influenza virus antigens, namely H1N1, H3N2 and Flu B.

2. Influenza pandemic. Influenza pandemic is caused by the antigen conversion due to the rearrangement of influenza virus genes. Such influenza pandemic shows great harm to the society, because human seldom develops immunity against such mutation in such big segment in the genome. In the last century there were three outbreaks of such influenza pandemic, and each outbreak resulted in a great number of infections and deaths, and caused great loss to the economics as well as to the society. As estimated the "Spanish Influenza" (Span flu), one of the most severe natural calamities in the history, happened during 1918-1920, infected about 500 million people (one third of the world population), and killed 40-50 million which was 3% of the world population then. Thereafter, "Asian influenza" and "Hongkong influenza" took place in 1957 and 1968, and also caused millions of cases of death. With the development of the society, the communications between countries and districts has been becoming more and more convenient and frequent, which has also facilitated the spreading of influenza pandemic. WHO believes in the past it takes 6-9 months for an influenza pandemic to spread over the world but now only 3 months is needed. It is estimated that in developed counties, the next influenza pandemic will bring 130 million outpatients, 2 million inpatients, and 650 thousand deaths. In developing countries the influence would be more severe, and there would even be millions of deaths. Therefore, such influenza pandemic would be great risks to global public health. The H1N1 influenza in 2009 has also been paid great attention by WHO and different national health authorities because it shows characters of an influenza pandemic.

3. Bird Influenza. This infection is caused by mutant bird virus. Although no outbreak has been observed in human population, the extremely high fatality rate has brought great risks to human health. Also, such highly pathogenic avian influenza could hardly get controlled because the wild hosts thereof migrate continuously, so it has brought new challenges to global public health. WHO has reported 492 cases up to Mar. 30, 2010, and there have been 291 deaths (the data comes from the website of the Chinese Center of Disease Control Office of Emergency.

The public health offices of different countries has made efforts to defend against such danger, and WHO has set up a global monitoring network and hopes alarms could be made according to such monitoring. Until now, the most effective way to control spreading of infectious diseases is vaccine. Especially in influenza virus, influenza vaccine immunization is the most effective means to prevent and control the spreading of influenza virus. Although the three types of influenza spreading are correspond to different marketed vaccines, current vaccines only protect the object from being infected by the influenza viruses which are identical or similar to the vaccine strain, and are unlikely to overcome the mutation of viruses to prevent the infection caused by multiple or different influenza viruses from vaccine strains. Therefore, the candidate vaccine strains for seasonal influenza viruses in each influenza season would be reappraised by WHO according to the spreading trend, and the vaccine strains would be renewed every year. The vaccine strains selected may be not matched with the seasonal spreading virus strains, and there are risks in the effect of the vaccine.

As indicated by reported data, influenza virus hemagglutinin (HA) protein is a protective antigen, which protects the host by inducing neutralizing antibody (nAb). Therefore, the influenza vaccines are evaluated on the HA content, and the effect for the vaccine is evaluated by the titer of hemagglutination inhibition antibodies. As well known by people skilled in the art, HA is the protein with most mutations in A-flu. Until now there has been 16 subtypes of HA discovered, and the antigenicity between the HA antigens are not the same. Although the protection related epitopes are mostly found in HA, and current vaccines may induce antibodies with high titer, however, the epitopes with high immunogenicity changes all the time. A vaccine is only effective against the virus strain it is identical to or the similar strains, and does not show broad protection ability against other strains or new strains. Essentially, the current vaccine technology does not overcome the mutation among the virus strains to archive a broad, cross protection.

Also it is expected to obtain a vaccine with broad protection ability, and retain strong protection against Influenza A, subtype H1. In 2009, H1N1 influenza has spread around the world and has caused many deaths. The protection ability against H1 influenza is thus an important scale for a vaccine.

DESCRIPTION OF THE INVENTION

In this invention, the phrase "shared sequences" is used interchangeably with "consensus sequences", and "hemagglutinin" is used interchangeably with "HA".

This invention provides a new type of combinatorial vaccine against influenza virus and the combinatorial method thereof. In the invention a number of different influenza vaccines are combined in a sequence to obtain new characters which could not be archived by single vaccine or the mixture of said vaccines. The key point of the invention is to use different influenza virus HA antigens to inoculate in a certain sequence to induce neutralizing antibodies against a number of influenza viruses.

The inventors has filed a patent application named "A combinatorial vaccine against multiple AIDS viruses and a combinatorial method thereof" (Application Number: CN 200910027615.2) on May 25 2009, in which the principle of sequential inoculation was described. In this invention the principle has been applied on influenza vaccines.

This invention provides a universal type influenza immune method against multiple influenza viruses, characterized in that two or more different influenza vaccines are inoculated by a certain sequence, and each influenza vaccine is inoculated at least once, and the inoculations take place two or more times; wherein each influenza vaccine includes one or more antigens, the immunogenic fragments thereof, or the coding genes thereof, and further includes a different antigen, the immunogenic fragments of the different antigen, or the coding gene of the different antigen. Preferably, the antigen is influenza virus hemagglutinin protein (HA).

In a preferable aspect of the invention, the influenza vaccines in the invention may be selected from: inactivated vaccines, attenuated vaccines, recombinant HA subunit vaccines, DNA vaccines carrying influenza virus hemagglutinin coding genes, recombinant virus carrier vaccine, recombinant bacteria carrier vaccine or recombinant yeast carrier vaccine, recombinant virus-like particle vaccines which express hemagglutinin, and a combination of the vaccines above.

In a preferable aspect of the invention, the said HA is selected from the HA of H1, H2, H3, H4, H5, H6, H7, H8, H9, H10, H11, H12, H13, H14, H15, and H16 subtype of influenza A, and the HA of influenza B.

In a preferable aspect of the invention, the said HA is selected from the HA of H1, H3, H5 subtype of influenza A and the HA of influenza B.

In a preferable aspect of the invention, the said HA is selected from the HA of H1, H3, and H5 subtype of influenza A. Preferably, the two or more influenza vaccines comprise one or more HA or the coding genes thereof from H1 subtype.

In a preferable aspect of the invention, the influenza virus hemagglutinin protein comes from A or B type influenza virus, or is from different subtypes of an influenza virus, and the said subtypes include, but are not limited to H1N1, H3N2, H5N1 or H7N7; or is from the different hemagglutinin protein types from one virus strain, such as HA1 or HA2 from a same virus strain. The influenza virus hemagglutinin protein may be selected from HA0, HA1, HA2 or the immunogenic fragments thereof. The influenza virus hemagglutinin coding gene may be codon-usage optimized for human.

In a specially appointed Example, the influenza virus hemagglutinin protein is selected from the H1, H2, H3, H4, H5, H6, H7, H8, H9, H10, H11, H12, H13, H14, H15, and H16 subtype of influenza A or the hemagglutinin protein of influenza B or the combination thereof; preferably, hemagglutinin proteins of H1, H3 or H5 subtype of influenza A.

More preferably, the influenza virus hemagglutinin proteins are the shared sequences or ancestral sequences of the same subtype.

In a preferred aspect of the invention, an immunization method is provided, and three immunizations are carried out in sequence, and a) the first immunization is H1 vaccine in which the HA is from H1 subtype of influenza A; b) the second immunization is H3 vaccine in which the HA is from H3 subtype of influenza A; and c) the third immunization is H5 vaccine in which the HA is from H5 subtype.

In a further preferred aspect of the invention, an immunization method is provided, and the HA of H1 vaccine is from A/Texas/05/2009(H1N1), and the HA of H3 vaccine is the shared sequence of the H3 subtype of 2006 to 2009, and the HA of H5 vaccine is the shared sequence of the H5 subtype of 2006 to 2009.

In a still further preferred aspect of the invention, an immunization method is provided, and the H1 vaccine is pVAX1-TE09 H1, and the H3 vaccine is pVAX1-CON H3, and the H5 vaccine is pVAX1-CON H5; wherein pVAX1-TE09 H1 is a recombinant DNA vaccine expressing the HA of the influenza virus A/Texas/05/2009(H1N1) strain, pVAX1-CON H3 is a recombinant DNA vaccine expressing the shared sequence of H3 subtype HA of 2006 to 2009, and pVAX1-CON H5 is a recombinant DNA vaccine expressing the shared sequence of H5 subtype HA of 2006 to 2009.

In a preferred aspect of the invention, an immunization method is provided, and three immunizations are carried out in sequence, and all the immunizations are H1 vaccine in which the HA is from H1 subtype of influenza A.

In a further preferred aspect of the invention, an immunization method is provided, and the HAs of H1 vaccine are from A/Brisbane/59/2007(H1N1), A/Brisbane/59/2007 (H1N1), and A/Texas/05/2009(H1N1).

In a still further preferred aspect of the invention, an immunization method is provided, and the three H1 vaccines are pVAX1-BR07 H1, pVAX1-BR07 H1, and rvv-TE09 H1; wherein pVAX1-BR07 H1 is a recombinant DNA vaccine expressing the HA of the influenza virus A/Brisbane/59/2007(H1N1) strain, and rvv-TE09 H1 is a recombinant vaccinia virus vector vaccine expressing the HA of influenza virus A/Texas/05/2009(H1N1) strain.

In a preferred aspect of the invention, four immunizations are carried out in sequence, and a) the first immunization is BHA vaccine in which the HA is from influenza B; b) the second immunization is H1 vaccine in which the HA is from H1 subtype of influenza A; c) the third immunization is H3 vaccine in which the HA is from H3 subtype of influenza A; and d) the forth immunization is H5 vaccine in which the HA is from H5 subtype.

In an further preferred aspect of the invention, an immunization method is provided, and the HA of BHA vaccine is from B/Brisbane/60/2008, the HA of H1 vaccine is from A/Texas/05/2009(H1N1), and the HA of H3 vaccine is the shared sequence of the H3 subtype of 2006 to 2009, and the HA of H5 vaccine is the shared sequence of the H5 subtype of 2006 to 2009.

In a still further preferred aspect of the invention, an immunization method is provided, and the BHA vaccine is pVAX1-BR08 BHA, the H1 vaccine is pVAX1-TE09 H1, and the H3 vaccine is pVAX1-CON H3, and the H5 vaccine is pVAX1-CON H5; wherein pVAX1-BR08 is a recombinant DNA vaccine expressing the HA of B/Brisbane/60/2008, pVAX1-TE09 H1 is a recombinant DNA vaccine expressing the HA of the influenza virus A/Texas/05/2009 (H1N1) strain, pVAX1-CON H3 is a recombinant DNA vaccine expressing the shared sequence of H3 subtype HA of 2006 to 2009, and pVAX1-CON H5 is a recombinant DNA vaccine expressing the shared sequence of H5 subtype HA of 2006 to 2009.

The immune method against influenza of the invention may be aimed at birds or mammals, preferably human.

In the immune method against influenza of the invention the interval between two inoculations is at least 1 week; preferably 2 or more weeks, up to 4 weeks.

In another aspect of the invention, influenza combinatorial vaccines for any of the above influenza immune methods are provided, which comprise two or more influenza vaccines for sequential inoculation, characterized in that each influenza vaccine includes one or more antigens, the immunogenic fragments thereof, or the coding genes thereof, and further includes a different antigen, the immunogenic fragments of the different antigen, or the coding gene of the different antigen. The two or more influenza vaccines are inoculated by a certain sequence, and each influenza vaccine is inoculated at least once, and the inoculations take place two or more times. Preferably, the antigen is influenza virus HA, or a combination of influenza virus HAs.

In a preferred aspect of the invention, the two or more influenza vaccines are selected from: inactivated vaccines, attenuated vaccines, recombinant HA subunit vaccines, DNA vaccines carrying influenza virus HA coding genes, recombinant virus carrier vaccines, recombinant bacteria carrier vaccines or recombinant yeast carrier vaccines, recombinant virus-like particle vaccines which express HA, or a combination of the vaccines above. Any above vaccine contains influenza virus HA antigen, the immunogenic fragments thereof or the coding gene thereof. Preferably, the said HA is selected from the HA of H1, H2, H3, H4, H5, H6, H7, H8, H9, H10, H11, H12, H13, H14, H15, or H16 subtype of influenza A and the HA of influenza B.

In another preferred aspect of the invention, the two or more influenza vaccines comprise one or more HA or the coding genes thereof from H1 subtype.

In another preferred aspect of the invention, the influenza virus HA is selected from HA0, HA1 HA2 or the immunogenic fragments thereof.

In a preferred aspect of the invention, the said HA sequences are the shared sequences or ancestral sequences of the same subtype.

In a preferred aspect of the invention, the said HA coding genes are codon-usage optimized for human.

In an aspect of the invention, four immunizations are carried out in sequence, and a) the first immunization is BHA vaccine in which the HA is from influenza B; b) the second immunization is H1 vaccine in which the HA is from H1 subtype of influenza A; c) the third immunization is H3 vaccine in which the HA is from H3 subtype of influenza A; and d) the forth immunization is H5 vaccine in which the HA is from H5 subtype.

In a preferable aspect of the invention, the HA of BHA vaccine is from B/Brisbane/60/2008, the HA of H1 vaccine is from A/Texas/05/2009(H1N1), and the HA of H3 vaccine is the shared sequence of the H3 subtype of 2006 to 2009, and the HA of H5 vaccine is the shared sequence of the H5 subtype of 2006 to 2009.

In an aspect of the invention, three immunizations are carried out in sequence, and a) the first immunization is H1 vaccine in which the HA is from H1 subtype of influenza A; b) the second immunization is H3 vaccine in which the HA is from H3 subtype of influenza A; and c) the third immunization is H5 vaccine in which the HA is from H5 subtype.

In a preferred aspect of the invention, the HA of H1 vaccine is from A/Texas/05/2009(H1N1), and the HA of H3 vaccine is the shared sequence of the H3 subtype of 2006 to 2009, and the HA of H5 vaccine is the shared sequence of the H5 subtype of 2006 to 2009.

In a preferred aspect of the invention, three immunizations are carried out in sequence, and all the immunizations are H1 vaccine in which the HA is from H1 subtype of influenza A.

In a preferred aspect of the invention, the HAs of H1 vaccines are from A/Brisbane/59/2007(H1N1), A/Brisbane/59/2007(H1N1), and A/Texas/05/2009(H1N1).

In a preferred aspect of the invention, the vaccine is aimed at mammals, preferably human.

The invention further provides the use of any of the influenza combinatorial vaccines in preventing or treating influenza virus infection.

In another aspect of the invention, the use of any of the influenza combinatorial vaccines in the manufacture of a medicament for preventing or treating influenza virus infection is provided.

With regard to the influenza viruses with multiple subtypes, and abundant mutations among the subtypes, inoculating the subject one or more times with an immunogen from one strain or inoculating the subject once with multiple immunogens from multiple stains do not provide a cross protection with a broad spectrum. By using immunogens from two or more strains to inoculate in a sequence, the common or consensus epitopes (epitopes shared by two or more strains) are preferentially activated, and the immune response to such epitopes is enhanced in subsequent vaccination. Such immune response is considered to be a cross immune response with a broad spectrum, and shows resistance to the two or more strains inoculated. Considering the fact that the common or consensus epitopes are critical to viruses with high mutation potential and does not easily change, the combinatorial vaccine also shows resistance to other uninoculated or new strains.

Another advantage of the invention is that the combinatorial vaccine in this invention shows very strong protection against various H1 influenza viruses. As indicated in the examples below, the combinatorial vaccines show stronger to most of the conventional virus H1, and thus are useful in inoculating against such frequently occurred infection.

EXAMPLES

In this invention influenza vaccines carrying HA antigens or HA coding genes from different influenza subtypes or different strains of the same subtype are inoculated in sequence to give a combinatorial vaccine, and thus neutralizing antibodies with a broad spectrum is obtained, so as to prevent infection of influenza.

In this invention, the first injection may carry the antigen from H1-16 of any subtype strains of influenza-A or HA of influenza-B, or a combination of one or more of the above; preferably, the antigen is selected from H1, H3, H5 subtype of influenza-A. The second injection may carry the antigen from H1-16 of any subtype strains of influenza-A or HA of influenza-B, or a combination of one or more of the above; preferably, the antigen is selected from H1, H3, H5 subtype of influenza-A, and at least one HA in the second injection is different from the first injection.

The influenza combinatorial vaccine may include a third injection of vaccine, and the third injection may carry the antigen from H1-16 of any subtype strains of influenza-A or HA of influenza-B, or a combination of one or more of the above; preferably, the antigen is selected from H1, H3, H5 subtype of influenza-A, and at least one HA in the third injection is different from the first or second injection.

The influenza combinatorial vaccine may include additional injection of vaccine, the forth or even more injection may carry the antigen from H1-16 of any subtype strains of influenza-A or HA of influenza-B, or a combination of one or more of the above; preferably, at least one HA in the additional injection is different from the previous injection.

In this invention following animals, virus strains, vaccines and chemicals have been used:

DNA Vaccine Construction and Preparation.

Influenza strain A/Texas/05/2009(H1N1) HA (Genbank ACP41934) (TE09 H1) amino acid sequence (as shown in SEQ ID NO:1) was codon-usage optimized and the codon-usage optimized nucleotide sequence (as shown in SEQ ID NO:2) was synthesized chemically by Generay biotechnology. Then the nucleotide sequence was transferred to the DNA vaccine vector pVAX1 (Invitrogen, V260-20, CA, USA) by well known molecular biology methods. The constructed plasmid DNA vaccine was named pVAX1-TE09 H1 herein and confirmed by sequencing (Invitrogen, Shanghai, China). Batch production of the vaccine was prepared by Endo-free Plasmid Giga Kits (QIAGEN, GE).

The common sequence of the influenza virus H3 subtype of 2006 to 2009 Influenza strain (CON H3) amino acid sequence (as shown in SEQ ID NO:3) was codon-usage optimized and the codon-usage optimized nucleotide sequence (as shown in SEQ ID NO:4) was synthesized chemically by Generay biotechnology. Then the nucleotide sequence was transferred to the DNA vaccine vector pVAX1 (Invitrogen, V260-20, CA, USA) by well known molecular biology methods. The constructed plasmid DNA was named pVAX1-CON H3 herein and confirmed by sequencing (Invitrogen, Shanghai, China). Batch production of the vaccine was prepared by Endo-free Plasmid Giga Kits (QIAGEN, GE).

The other DNA vaccines used in the invention could be constructed and prepared according to the above methods. BR07 H1 (the amino acid sequence shown in SEQ ID NO:5, and the nucleic acid sequence shown in SEQ ID NO:6), BR07 H3 (the amino acid sequence shown in SEQ ID NO:7, and the nucleic acid sequence shown in SEQ ID NO: 8). CON H5 (the amino acid sequence shown in SEQ ID NO:9, and the nucleic acid sequence shown in SEQ ID NO:10), BR08 BHA (the amino acid sequence shown in SEQ ID NO:11, and the nucleic acid sequence shown in SEQ ID NO:12) are all employed to construct the vaccines. The amino acid sequences and nucleic acid sequences are shown in the Sequence Listing.

All DNA vaccines used herein were constructed and prepared by the inventors as following protocols.

All HA antigen sequences were codon-usage optimized and synthesized by Generay biotechnology. Then the antigen sequences were transferred to the DNA vaccine vector pVAX1 (Invitrogen, V260-20, CA, USA) by well-known molecular biology methods. Constructed DNA vaccines were confirmed by sequencing (Invitrogen, Shanghai, China) and HA expression of the DNA vaccines were confirmed by Western Blotting. All constructed DNA vaccines were prepared by Endo-free Plasimd Giga Kits (QIAGEN).

Recombinant Vaccinia Vector Vaccine Construction and Preparation.

All recombinant vaccinia vector vaccines used herein were constructed and prepared by the inventors as well known protocols (Fred M. Ausubel, et al. Current Protocols in Molecular Biology, 2002). All recombinant vaccinia vector vaccines were prepared and titrated in Vero cells (Cell Research Center of Shanghai Institutes for Biological Sciences, Shanghai).

Animals and Immunization.

SPF female BAL B/c mice were purchased from Slac laboratory animal (Shanghai) and maintained in the laboratory animal center of Soochow University. All immunizations are performed by intramuscular injection.

Pseudotype-Based Neutralization Assay.

Pseudotyped virus assay is employed to evaluate the protective effect of the combinatorial vaccines on different strains of influenza viruses as a common accepted protocol. The method has been well described in the Wei et al. Science 27 Aug. 2010: 329 (5995), 1060-1064.

In the invention, pseudotyped virus was prepared by the following protocol. $5 \times 10^6$ 293 T (Cell Research Center of Shanghai Institutes for Biological Sciences, Shanghai) packaging cells were co-transfected with 5 μg lentivirus vector pNL4-3 luc. R-E- and 2.5 μg HA expression plasmid and 2.5 μg NA expression plasmid using Turbofect (Fermentas).

All HA and NA were was synthesized chemically by Generay biotechnology. All expressing plasmids were constructed and prepared according to the above methods. After overnight incubation, cells were washed once with phosphate buffered saline (PBS) and cultured in 5 ml of complete DMEM (Hyclone) for 16 to 20 hours. The pseudotyped virus supernatants were harvested and stored at −80° C. freezer in aliquots until used in a neutralization assay. HA coding DNAs from 13 strains are employed in the embodiments. The NA was from A/Shanghai/37T/2009 (H1N1) (GenBank No. ACS27784).

The HA coding sequences of the pesudotyped virus, and the expressed protein sequences thereof are listed as follows:

1) A/Singapore/6/1986(H1N1) HA (GenBank No. ABO38395)

The DNA sequence is shown in SEQ ID NO:13, and the expressed amino acid sequence is shown in SEQ ID NO:14.

2) A/NewCaledonia/20/1999(H1N1) HA (GenBank No. AY289929)

The DNA sequence is shown in SEQ ID NO:15, and the expressed amino acid sequence is shown in SEQ ID NO:16.

3) A/SolomonIslands/3/2006(H1N1) HA (GenBank No. ABU99109)

The DNA sequence is shown in SEQ. ID. No. SEQ ID NO:17, and the expressed amino acid sequence is shown in SEQ ID NO:18.

4) A/Brisbane/59/2007(H1N1) HA (GenBank No. ACA28844)

The DNA sequence is shown in SEQ ID NO:19, and the expressed amino acid sequence is shown in SEQ ID NO:20.

5) A/Texas/05/2009(H1N1) HA (GenBank No. ACP41934)

The DNA sequence is shown in SEQ ID NO:2, and the expressed amino acid sequence is shown in SEQ ID NO:1.

6) A/Moscow/10/1999(H3N2) HA (GenBank No. AAT08002)

The DNA sequence is shown in SEQ ID NO:21, and the expressed amino acid sequence is shown in SEQ ID NO:22.

7) A/Fujian/411/2002(H3N2) HA (GenBank No. ABB71825)

The DNA sequence is shown in SEQ ID NO:23, and the expressed amino acid sequence is shown in SEQ ID NO:24.

8) A/Wisconsin/67/2005(H3N2) HA (GenBank No. ACF54576)

The DNA sequence is shown in SEQ ID NO:25, and the expressed amino acid sequence is shown in SEQ. ID. No. SEQ ID NO:26.

9) A/Brisbane/10/2007(H3N2) HA (GenBank No. ABW23353)

The DNA sequence is shown in SEQ ID NO:27, and the expressed amino acid sequence is shown in SEQ ID NO:28.

10) A/VietNam/1203/2004(H5N1) (GenBank No. AAW80717)

The DNA sequence is shown in SEQ ID NO:29, and the expressed amino acid sequence is shown in SEQ ID NO:30.

11) A/duck/Novosibirsk/56/2005(H5N1) HA (GenBank No. ABB43059)

The DNA sequence is shown in SEQ ID NO:31, and the expressed amino acid sequence is shown in SEQ ID NO:32.

12) B/Brisbane/60/2008(Victoria lineage) HA (GenBank No. ACN29380)

The DNA sequence is shown in SEQ ID NO:33, and the expressed amino acid sequence is shown in SEQ ID NO:34.

13) B/Florida/4/2006(Yamagata lineage Yamagata lineage) HA (GenBank No. ACA33493)

The DNA sequence is shown in SEQ ID NO:35, and the expressed amino acid sequence is shown in SEQ ID NO:36.

14) A/Shanghai/37T/2009(H1N1) HA (GenBank No. ACS22784)

The DNA sequence is shown in SEQ ID NO:37, and the expressed amino acid sequence is shown in SEQ ID NO:38.

Names of the pseudotyped virus and the HA expressing plasmid, Influenza strain and GenBank Accession number thereof are shown below in Table 1.

TABLE 1

| pseudotyped virus | HA expressing plasmid | Influenza strain | GenBank No. |
|---|---|---|---|
| SI86 H1pp | pVAX-SI86 H1 | A/Singapore/6/1986 (H1N1) | CY020477.1 |
| NC99 H1pp | pVAX-NC99 H1 | A/NewCaledonia/20/1999 (H1N1) | AY289929.1 |
| SI06 H1pp | pVAX-SI06 H1 | A/SolomonIslands/3/2006 (H1N1) | EU124177.1 |
| BR07 H1pp | pVAX-BR07 H1 | A/Brisbane/59/2007 (H1N1) | CY030230.1 |
| TE09 H1pp | pVAX-TE09 H1 | A/Texas/05/2009 (H1N1) | ACP41934 |
| MO99 H3pp | pVAX-MO99 H3 | A/Moscow/10/1999 (H3N2) | AY531035.1 |
| FJ02 H3pp | pVAX-FJ02 H3 | A/Fujian/411/2002 (H3N2) | DQ227423.1 |
| WI05 H3pp | pVAX-WI05 H3 | A/Wisconsin/67/2005 (H3N2) | CY034116.1 |
| BR07 H3pp | pVAX-BR07 H3 | A/Brisbane/10/2007 (H3N2) | EU199366.1 |
| VN04 H5pp | pVAX-VN04 H5 | A/Viet Nam/1203/2004 (H5N1) | AY818135.1 |
| NV05 H5pp | pVAX-NV05 H5 | A/duck/Novosibirsk/56/2005 (H5N1) | DQ230522.1 |
| BR08 BHApp | pVAX-BR08 BHA | B/Brisbane/60/2008 (Victoria lineage) | FJ766840.1 |
| FI06 BHApp | pVAX-FI06 BHA | B/Florida/4/2006 (Yamagata-lineage) | EU515992.1 |

Madin Darby Canine Kidney (MDCK) cells (Cell Research Center of Shanghai Institutes for Biological Sciences, Shanghai) were cultured overnight in 96 well plates in complete DMEM, sera samples were 2 or 3-fold serially diluted and incubated with indicated amounts of pseudotyped virus at the final volume of 150 μL at 37° C. for 1 hour. The mixture was added to cultures of MDCK cells. After the overnight incubation, cells were then washed with phosphate buffered saline (PBS) and cultured in complete DMEM medium for 48 hours. Luciferase activity (RLA) was measured by a BrightGlo Luciferase assay according to the manufacturer's instruction (Promega, Madison, Wis.). In the assay, the neutralizing titer of serial dilutions of mouse sera was obtained by determining percent inhibition of transduction efficiency in MDCK cells transduced with pseudotyped viruses. Percent inhibition was calculated as follows: (RLA in pseudotypes and medium control—RLA in pseudotypes and serum in a given dilution)/RLA in pseudotypes and medium control. The 50% Inhibitory concentration (IC50) was reported as the dilutions of a given serum that result in 50% reduction of luciferase activity.

Example 1

In the first immune injection (100 μm/mice intramuscular) the recombinant DNA vaccine pVAX1-TE09 H1 is used, wherein the pVAX1-TE09 H1 is from influenza strain A/Texas/05/2009(H1N1) HA (Genbank No. ACP41934). Then a recombinant DNA vaccine pVAX1-CON H3 expressing the shared sequence of the influenza virus H3 subtype of 2006 to 2009 and a recombinant DNA vaccine pVAX1-CON H5 expressing the shared sequence of the influenza virus H5 subtype of 2006-2009 are used in the second and third immune injection in 4-6 week female BALB/C mice (10 mice in each group). The vaccines employed are called combinatorial vaccine 1 bellow, and are shown in detail in table 2. Two weeks after the last injection, blood serum is collected and pseudovirus neutralization assay are carried out. The protocol of the pseudovirus neutralization assay is listed above.

TABLE 2

An outline of the immune injections in Example 1

| | Injection 1 (Week 0) | Injection 2 (Week 2) | Injection 3 (Week 4) |
|---|---|---|---|
| Control 1 | pVAX1 | pVAX1 | pVAX1 |
| Conventional vaccine 1 | pVAX1-TE09 H1 | pVAX1-TE09 H1 | pVAX1-TE09 H1 |

TABLE 2-continued

An outline of the immune injections in Example 1

| | Injection 1 (Week 0) | Injection 2 (Week 2) | Injection 3 (Week 4) |
|---|---|---|---|
| Combinatorial vaccine 1 | pVAX1-TE09 H1 | pVAX1-CON H3 | pVAX1-CON H5 |

The results show that conventional vaccine 1 produces high level neutralizing antibody against the strain A/Texas/05/2009(H1N1) (the GMT is 14400.0) and the combinatorial vaccine 1 also produces high level neutralizing antibody against the strain (the GMT is 3200.0). With regard to different strains of the same subtype, A/Brisbane/59/2007 (H1N1) obviously the conventional vaccine 1 does not activate the cross reactivity or the activation is rather poor (the GMT is 25.0), however the combinatorial vaccine still shows some activity (the GMT is 100.0), and the activity is one to four times stronger than the conventional vaccine. Similarly, with regard to the different strains A/Solomon Islands/3/2006(H1N1) and A/Singapore/6/1986(H1N1), the combinatorial vaccine produces cross neutralizing antibodies better. The combinatorial vaccine also performs better for H3 and H5 subtypes. In one word, the combinatorial vaccine is able to activate neutralizing antibodies with a broad spectrum which blocks the infection of a number of influenza viruses.

TABLE 3

The Testing results of the neutralizing antibodies in Example 1

|  | Control 1 (GMT Value) | Conventional vaccine 1 (GMT Value) | Combinatorial vaccine 1 (GMT Value) |
|---|---|---|---|
| TE09 H1pp | 5.0 | 14400.0 | 3200.0 |
| BR07 H1pp | 25.0 | 25.0 | 100.0 |
| SI86 H1pp | 10.0 | 10.0 | 270.0 |
| NC99 H1pp | 5.0 | 5.0 | 90.0 |
| SI06 H1pp | 25.0 | 70.7 | 565.7 |
| BR07 H3pp | 60.0 | 120.0 | 7290.0 |
| VN04 H5pp | 37.5 | 50.0 | 800.0 |

Example 2

In the first and second immune injection the recombinant DNA vaccine pVAX1-BR07 H1 is used (100 µg/mice), wherein the HA sequence is from influenza strain A/Brisbane/59/2007(H1N1)(Gebank ACA28844). Then a vaccinia virus vector vaccine pVAX1-BR07 H1 expressing the homogenetic HA (A/Brisbane/59/2007(H1N1)) is provided as a second injection (called the conventional vaccine below). Another vaccinia vaccine rvv-TE09 H1 expressing the HA from influenza strain A/Texas/05/2009(H1N1) is used as a third injection in the combinatorial vaccine group. All vaccinia vaccines in the example are intramuscularly vaccinated in each mouse in a dose of $5 \times 10^6$ PFU. An outline of the immunization schedule is shown in detail in table 4.

Four weeks after the last injection, serum of all immunized mice is collected and neutralization tests are carried out. The detail of the neutralization test has been described in the example 1. The pseudovirus includes a strain used in the immune injection, BR07 H1pp, TE09 H1pp; a different strain of the same subtype, SI06 H1pp, SI86 H1pp, NC99 H1pp; and a different strain from a different subtype, VN04 H5pp.

TABLE 4

An outline of the immune injections in Example 2

|  | DNA Vaccine | | vaccinia virus vector vaccine |
|---|---|---|---|
|  | Injection 1 (Week 0) | Injection 2 (Week 2) | Injection 3 (Week 4) |
| Control 2 | pVAX1 | pVAX1 | rvv-WT |
| Conventional vaccine 2 | pVAX1-BR07 H1 | pVAX1-BR07 H1 | rvv-BR07 H1 |
| Combinatorial vaccine2 | pVAX1-BR07 H1 | pVAX1-BR07 H1 | rvv-TE09 H1 |

The combinatorial vaccine effectively produces neutralizing antibodies against many influenza virus strains (See table 4). The BR07 H1 component in the conventional is highly similar to SI06 H1 and NC99 H1, and the conventional vaccine thus produces neutralizing antibodies against these two strains (the GMT values are 360.0 and 810.0 respectively). However, with regard to the strain A/Texas/05/2009(H1N1) of the same subtype, the conventional vaccine does not produce neutralizing antibodies (the GMT is 5.0), while the combinatorial vaccine produces high level of neutralizing antibodies (the GMT is 14400.0) much better than the conventional vaccine and the control.

TABLE 5 the neutralizing antibody tests in Example 2

|  | Control 2 (GMT Value) | Conventional Vaccine 2 (GMT Value) | Combinatorial vaccine2 (GMT Value) |
|---|---|---|---|
| TE09 H1pp | 5.0 | 5.0 | 14400.0 |
| BR07 H1pp | 25.0 | 910.5 | 416.2 |
| SI06 H1pp | 30.0 | 1018.2 | 360.0 |
| SI86 H1pp | 5.0 | 30.0 | 10.0 |
| NC99 H1pp | 5.0 | 810.0 | 810.0 |

Example 3

In the first immune injection the recombinant DNA vaccine pVAX1-BR08 BHA is used (100 µg/mice), wherein the HA sequence is from influenza strain B/Brisbane/60/2008 (GenBank No. ACN29380). In the second immune injection the recombinant DNA vaccine pVAX1-TE09 H1 is used, wherein the pVAX1-TE09 H1 is from influenza strain A/Texas/05/2009(H1N1) HA (GenBank No. ACP41934). Then the recombinant DNA vaccine pVAX1-CON H3 expressing the shared sequence of the influenza virus H3 subtype of 2006 to 2009 and subsequently the last recombinant DNA vaccine pVAX1-CON H5 expressing the shared sequence of the influenza virus H5 subtype of 2006 to 2009 are used in the third and forth immune injection in 4-6 week female Bal B/c mice (10 mice in each group) respectively. An outline of the immunization schedule is shown in detail in table 6.

Four weeks after the last injection, serum of all immunized mice is collected and neutralization tests are carried out. The detail of the neutralization test has been described in the example 1. The pseudovirus includes SI86 H1pp, NC99 H1pp, SI06 H1pp, TE09 H1pp, BR07 H1pp, MO99 H3pp, FJ02 H3pp, WI05 H3pp, BR07 H3pp, VN04 H5pp, BR08 BHApp, FI06 BHApp.

The results suggest that the combinatorial vaccine effectively produces potent neutralizing antibodies against many influenza virus strains than control (See table 7).

TABLE 6

An outline of the immune injections in Example 3

|  | DNA Vaccine | | | |
|---|---|---|---|---|
|  | Injection 1 (Week 0) | Injection 2 (Week 4) | Injection 3 (Week 8) | Injection 4 (Week 8) |
| Control 3 | pVAX1 | pVAX1 | pVAX1 | pVAX1 |
| Combinatorial vaccine 3 | pVAX 1-BR08 BHA | pVAX 1-TE09 H1 | pVAX1-CON H3 | pVAX1-CON H5 |

TABLE 7

The neutralizing antibody tests in Example 3

|  | Control 3 (GMT Value) | Combinatorial vaccine 3 (GMT Value) |
|---|---|---|
| SI86 H1pp | 25 | 32 |
| NC99 H1pp | 25 | 35 |
| SI06 H1pp | 25 | 122 |
| BR07 H1pp | 25 | 130 |
| TE09 H1pp | 25 | 2075 |
| MO99 H3pp | 25 | 77 |

TABLE 7-continued

The neutralizing antibody tests in Example 3

|  | Control 3 (GMT Value) | Combinatorial vaccine 3 (GMT Value) |
|---|---|---|
| FJ02 H3pp | 25 | 566 |
| WI05 H3pp | 25 | 3805 |
| BR07 H3pp | 25 | 4525 |
| VN04 H5pp | 25 | 519 |
| NV05 H5pp | 25 | 2975 |
| BR08 BHApp | 25 | 566 |
| FI06 BHApp | 25 | 25 |

The invention claimed is:

1. A universal influenza immunization method against multiple influenza strains, comprising inoculating a subject with two or more different influenza vaccines in a certain sequence, wherein the subject is inoculated with each influenza vaccine at least once, and the inoculations take place two or more times; wherein each influenza vaccine includes one or more antigens, the immunogenic fragments thereof, or the coding genes thereof, and further includes a different antigen, the immunogenic fragments of the different antigen, or the coding gene of the different antigen,
(i) wherein three immunizations are carried out in sequence, and
(a) the first immunization is an H1 vaccine in which the hemagglutinin (HA) is from an H1 subtype of influenza A;
(b) the second immunization is an H3 vaccine in which the HA is from an H3 subtype of influenza A;
(c) the third immunization is an H5 vaccine in which the HA is from an H5 subtype of influenza A;
(ii) wherein three immunizations are carried out in sequence, and all the immunizations are H1 vaccines in which the HA is from an H1 serotype influenza A; or
(iii) wherein four immunizations are carried out in sequence, and
(a) the first immunization is a BHA vaccine in which the HA is from influenza B;
(b) the second immunization is an H1 vaccine in which the HA is from an H1 subtype of influenza A;
(c) the third immunization is an H3 vaccine in which the HA is from an H3 subtype of influenza A; and
(d) the fourth immunization is an H5 vaccine in which the HA is from an H5 subtype of influenza A.

2. Method of claim 1, wherein the two or more influenza vaccines are selected from the group consisting of: inactivated vaccines, attenuated vaccines, recombinant HA subunit vaccines, DNA vaccines carrying HA coding genes, recombinant virus carrier vaccines, recombinant bacteria carrier vaccines or recombinant yeast carrier vaccines, recombinant virus-like particle vaccines which express HA, and a combination of the vaccines above.

3. Method of claim 1, wherein the two or more influenza vaccines comprise one or more HA or the coding genes thereof from an H1 subtype of influenza A.

4. Method of claim 1, wherein the said HA is selected from HA0, HA1, HA2 or the immunogenic fragments thereof.

5. Method of claim 1, wherein the amino acid sequences of said HA are the shared sequences or ancestral sequences of HA of the same influenza subtype.

6. Method of claim 1, wherein the influenza virus HA coding genes are codon-usage optimized for a human.

7. Method of claim 1, wherein the HA of the H1 vaccine is from A/Texas/05/2009(H1N1), and the HA of the H3 vaccine is the shared sequence of the H3 subtype of 2006 to 2009, and the HA of the H5 vaccine is the shared sequence of the H5 subtype of 2006 to 2009.

8. Method of claim 7, wherein the H1 vaccine is pVAX1-TE09 H1, and the H3 vaccine is pVAX1-CON H3, and the H5 vaccine is pVAX1-CON H5; wherein pVAX1-TE09 H1 is a recombinant DNA vaccine expressing the HA of the influenza virus A/Texas/05/2009(H1N1) strain, pVAX1-CON H3 is a recombinant DNA vaccine expressing the shared sequence of H3 subtype HA of 2006 to 2009, and pVAX1-CON H5 is a recombinant DNA vaccine expressing the shared sequence of H5 subtype HA of 2006 to 2009.

9. Method of claim 1, wherein the HAs of the H1 vaccine are from A/Brisbane/59/2007(H1N1), A/Brisbane/59/2007 (H1N1), and A/Texas/05/2009 (H1N1).

10. Method of claim 9, wherein the three H1 vaccines are pVAX1-BR07 H1, pVAX1-BR07 H1, and rvv-TE09 H1; wherein pVAX1-BR07 H1 is a recombinant DNA vaccine expressing the HA of the influenza virus A/Brisbane/59/2007(H1N1) strain, and rvv-TE09 H1 is a recombinant vaccinia virus vector vaccine expressing the HA of influenza virus A/Texas/05/2009(H1N1) strain.

11. Method of claim 1, wherein the HA of the BHA vaccine is from B/Brisbane/60/2008, the HA of H1 vaccine is from A/Texas/05/2009(H1N1), and the HA of H3 vaccine is the shared sequence of the H3 subtype of 2006 to 2009, and the HA of H5 vaccine is the shared sequence of the H5 subtype of 2006 to 2009.

12. Method of claim 11, wherein the BHA vaccine is pVAX1-BR08 BHA, the H1 vaccine is pVAX1-TE09 H1, and the H3 vaccine is pVAX1-CON H3, and the H5 vaccine is pVAX1-CON H5; wherein pVAX1-BR08 is a recombinant DNA vaccine expressing the HA of B/Brisbane/60/2008, pVAX1-TE09 H1 is a recombinant DNA vaccine expressing the HA of the influenza virus A/Texas/05/2009 (H1N1) strain, pVAX1-CON H3 is a recombinant DNA vaccine expressing the shared sequence of H3 subtype HA of 2006 to 2009, and pVAX1-CON H5 is a recombinant DNA vaccine expressing the shared sequence of H5 subtype HA of 2006 to 2009.

13. Method of claim 1, wherein the subject is a bird or a mammal or a human.

14. Method of claim 1, wherein the interval between two inoculations is at least 1 week, 2 or more weeks, or up to 4 weeks.

* * * * *

SEQUENCE LISTING

<160> NUMBER OF SEQ ID NOS: 38

<210> SEQ ID NO 1
<211> LENGTH: 566
<212> TYPE: PRT
<213> ORGANISM: Influenza Virus

<400> SEQUENCE: 1

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

```
Val His Asp Cys Asn Thr Thr Cys Gln Thr Pro Lys Gly Ala Ile Asn
    290                 295                 300
Thr Ser Leu Pro Phe Gln Asn Ile His Pro Ile Thr Ile Gly Lys Cys
305                 310                 315                 320
Pro Lys Tyr Val Lys Ser Thr Lys Leu Arg Leu Ala Thr Gly Leu Arg
                325                 330                 335
Asn Val Pro Ser Ile Gln Ser Arg Gly Leu Phe Gly Ala Ile Ala Gly
            340                 345                 350
Phe Ile Glu Gly Gly Trp Thr Gly Met Val Asp Gly Trp Tyr Gly Tyr
        355                 360                 365
His His Gln Asn Glu Gln Gly Ser Gly Tyr Ala Ala Asp Leu Lys Ser
    370                 375                 380
Thr Gln Asn Ala Ile Asp Glu Ile Thr Asn Lys Val Asn Ser Val Ile
385                 390                 395                 400
Glu Lys Met Asn Thr Gln Phe Thr Ala Val Gly Lys Glu Phe Asn His
                405                 410                 415
Leu Glu Lys Arg Ile Glu Asn Leu Asn Lys Lys Val Asp Asp Gly Phe
            420                 425                 430
Leu Asp Ile Trp Thr Tyr Asn Ala Glu Leu Leu Val Leu Leu Glu Asn
        435                 440                 445
Glu Arg Thr Leu Asp Tyr His Asp Ser Asn Val Lys Asn Leu Tyr Glu
    450                 455                 460
Lys Val Arg Ser Gln Leu Lys Asn Asn Ala Lys Glu Ile Gly Asn Gly
465                 470                 475                 480
Cys Phe Glu Phe Tyr His Lys Cys Asp Asn Thr Cys Met Glu Ser Val
                485                 490                 495
Lys Asn Gly Thr Tyr Asp Tyr Pro Lys Tyr Ser Glu Glu Ala Lys Leu
            500                 505                 510
Asn Arg Glu Glu Ile Asp Gly Val Lys Leu Glu Ser Thr Arg Ile Tyr
        515                 520                 525
Gln Ile Leu Ala Ile Tyr Ser Thr Val Ala Ser Ser Leu Val Leu Val
    530                 535                 540
Val Ser Leu Gly Ala Ile Ser Phe Trp Met Cys Ser Asn Gly Ser Leu
545                 550                 555                 560
Gln Cys Arg Ile Cys Ile
                565

<210> SEQ ID NO 2
<211> LENGTH: 1701
<212> TYPE: DNA
<213> ORGANISM: Influenza virus

<400> SEQUENCE: 2
atgaaggcca tcctggtggt gctgctgtac accttcgcca ccgccaacgc cgacaccctg      60
tgcatcggct accacgccaa caacagcacc gacaccgtgg acaccgtgct ggagaagaac     120
gtgaccgtga cccacagcgt gaacctgctg gaggacaagc acaacggcaa gctgtgcaag     180
ctgcgcggcg tggcccccct gcacctgggc aagtgcaaca tcgccggctg gatcctgggc     240
aaccccgagt gcgagagcct gagcaccgcc agcagctgga gctacatcgt ggagaccagc     300
agcagcgaca acggcacctg ctaccccggc gacttcatcg actacgagga gctgcgcgag     360
cagctgagca gcgtgagcag cttcgagcgc ttcgagatct tccccaagac cagcagctgg     420
cccaaccacg acagcaacaa gggcgtgacc gccgcctgcc ccacgccggc gccaagagc      480 ttctacaaga acctgatctg gctggtgaag aagggcaaca gctaccccaa gctgagcaag     540
```

-continued

```
agctacatca acgacaaggg caaggaggtg ctggtgctgt ggggcatcca ccaccccagc    600
accagcgccg accagcagag cctgtaccag aacgccgacg cctacgtgtt cgtgggcagc    660
agccgctaca gcaagaagtt caagcccgag atcgccatcc gccccaaggt gcgcgaccag    720
gagggccgca tgaactacta ctggaccctg gtggagcccg cgacaagat caccttcgag     780
gccaccggca acctggtggt gccccgctac gccttcgcca tggagcgcaa cgccggcagc    840
ggcatcatca tcagcgacac ccccgtgcac gactgcaaca ccacctgcca gacccccaag    900
ggcgccatca acaccagcct gcccttccag aacatccacc ccatcaccat cggcaagtgc    960
cccaagtacg tgaagagcac caagctgcgc ctggccaccg gctgcgcaa cgtgcccagc    1020
atccagagcc gcggcctgtt cggcgccatc gccggcttca tcgagggcgg ctggaccggc    1080
atggtggacg gctggtacgg ctaccaccac cagaacgagc agggcagcgg ctacgccgcc    1140
gacctgaaga gcacccagaa cgccatcgac gagatcacca caaggtgaa cagcgtgatc     1200
gagaagatga acacccagtt caccgccgtg ggcaaggagt caaccaccct ggagaagcgc    1260
atcgagaacc tgaacaagaa ggtggacgac ggcttcctgg acatctggac ctacaacgcc    1320
gagctgctgg tgctgctgga gaacgagcgc accctggact accacgacag caacgtgaag    1380
aacctgtacg agaaggtgcg cagccagctg aagaacaacg ccaaggagat cggcaacggc    1440
tgcttcgagt tctaccacaa gtgcgacaac acctgcatgg agagcgtgaa gaacggcacc    1500
tacgactacc ccaagtacag cgaggaggcc aagctgaacc gcgaggagat cgacggcgtg    1560
aagctggaga gcacccgcat ctaccagatc ctggccatct acagcaccgt ggccagcagc    1620
ctggtgctgg tggtgagcct gggcgccatc agcttctgga tgtgcagcaa cggcagcctg    1680
cagtgccgca tctgcatcta a                                               1701
```

<210> SEQ ID NO 3
<211> LENGTH: 566
<212> TYPE: PRT
<213> ORGANISM: Influenza virus

<400> SEQUENCE: 3

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160
```

```
Asn Ser Phe Phe Ser Arg Leu Asn Trp Leu Thr His Leu Lys Phe Lys
            165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Asn Asp Gln Ile
            195                 200                 205

Phe Leu Tyr Ala Gln Ala Ser Gly Arg Ile Thr Val Ser Thr Lys Arg
            210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
                260                 265                 270

Tyr Phe Lys Ile Arg Ser Gly Lys Ser Ser Ile Met Arg Ser Asp Ala
                275                 280                 285

Pro Ile Gly Lys Cys Asn Ser Glu Cys Ile Thr Pro Asn Gly Ser Ile
            290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
                355                 360                 365

Phe Arg His Gln Asn Ser Glu Gly Arg Gly Gln Ala Ala Asp Leu Lys
                370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
                435                 440                 445

Asn Gln His Thr Ile Asp Leu Thr Asp Ser Glu Met Asn Lys Leu Phe
                450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Glu Leu Lys Ser Gly Tyr Lys
                515                 520                 525

Asp Trp Ile Leu Trp Ile Ser Phe Ala Ile Ser Cys Phe Leu Leu Cys
                530                 535                 540

Val Ala Leu Leu Gly Phe Ile Met Trp Ala Cys Gln Lys Gly Asn Ile
545                 550                 555                 560

Arg Cys Asn Ile Cys Ile
                565
```

<210> SEQ ID NO 4
<211> LENGTH: 1701
<212> TYPE: DNA
<213> ORGANISM: influenza virus

<400> SEQUENCE: 4

```
atgaagacca tcatcgccct gagctacatc ctgtgcctgg tgttcgccca gaagctgccc      60
ggcaacgaca cagcaccgc caccctgtgc ctgggccacc acgccgtgcc caacggcacc     120
atcgtgaaga ccatcaccaa cgaccagatc gaggtgacca cgccaccga gctggtgcag     180
agcagcagca ccggcgagat ctgcgacagc ccccaccaga tcctggacgg cgagaactgc     240
accctgatcg acgccctgct gggcgacccc cagtgcgacg gcttccagaa caagaagtgg     300
gacctgttcg tggagcgcag caaggcctac agcaactgct accccctacga cgtgcccgac     360
tacgccagcc tgcgcagcct ggtggccagc agcggcaccc tggagttcaa caacgagagc     420
ttcaactgga ccggcgtgac ccagaacggc accagcagcg cctgcatccg ccgcagcaac     480
aacagcttct tcagccgcct gaactggctg acccacctga gttcaagta ccccgccctg     540
aacgtgacca tgcccaacaa cgagcagttc gacaagctgt acatctgggg cgtgcaccac     600
cccggcaccg acaacgacca gatcttcctg tacgcccagg ccagcggccg catcaccgtg     660
agcaccaagc gcagccagca gaccgtgatc cccaacatcg gcagccgccc ccgcgtgcgc     720
aacatcccca gccgcatcag catctactgg accatcgtga agcccggcga catcctgctg     780
atcaacagca ccggcaacct gatcgccccc cgcggctact tcaagatccg cagcggcaag     840
agcagcatca tgcgcagcga cgccccccatc ggcaagtgca cagcgagtg catcaccccc     900
aacggcagca tccccaacga caagcccttc cagaacgtga ccgcatcac ctacggcgcc     960
tgccccccgct acgtgaagca gaacaccctg aagctggcca ccggcatgcg caacgtgccc    1020
gagaagcaga cccgcggcat cttcggcgcc atcgccggct tcatcgagaa cggctgggag    1080
ggcatggtgg acggctggta cggcttccgc caccagaaca gcgagggccg cggccaggcc    1140
gccgacctga agagcaccca ggccgccatc gaccagatca cggcaagct gaaccgcctg    1200
atcggcaaga ccaacgagaa gttccaccag atcgagaagg agttcagcga ggtggagggc    1260
cgcatccagg acctggagaa gtacgtggag gacaccaaga tcgacctgtg gagctacaac    1320
gccgagctgc tggtggccct ggagaaccag cacaccatcg acctgaccga cagcgagatg    1380
aacaagctgt tcgagaagac caagaagcag ctgcgcgaga cgccgagga catgggcaac    1440
ggctgcttca gatctacca caagtgcgac aacgcctgca tcggcagcat ccgcaacggc    1500
acctacgacc acgacgtgta ccgcgacgag gccctgaaca ccgcttcca gatcaagggc    1560
gtggagctga gagcggcta caaggactgg atcctgtgga tcagcttcgc catcagctgc    1620
ttcctgctgt gcgtggccct gctgggcttc atcatgtggg cctgccagaa gggcaacatc    1680
cgctgcaaca tctgcatcta a                                              1701
```

<210> SEQ ID NO 5
<211> LENGTH: 565
<212> TYPE: PRT
<213> ORGANISM: Influenza vaccine

<400> SEQUENCE: 5

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30
```

-continued

Val Asp Thr Val Leu Glu Lys Asn Val Thr Val Thr His Ser Val Asn
        35                  40                  45

Leu Leu Glu Asn Ser His Asn Gly Lys Leu Cys Leu Leu Lys Gly Ile
50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr
        130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Lys Ala Leu Tyr
        195                 200                 205

His Thr Glu Asn Ala Tyr Val Ser Val Val Ser Ser His Tyr Ser Arg
        210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
        290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
        370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys

```
            450                 455                 460
Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
                500                 505                 510

Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 6
<211> LENGTH: 1698
<212> TYPE: DNA
<213> ORGANISM: Influenza virus

<400> SEQUENCE: 6
atgaaggtga agctgctggt gctgctgtgc accttcaccg ccacctacgc cgacaccatc      60
tgcatcggct accacgccaa caacagcacc gacaccgtgg acaccgtgct ggagaagaac     120
gtgaccgtga cccacagcgt gaacctgctg gagaacagcc acaacggcaa gctgtgcctg     180
ctgaagggca tcgccccccct gcagctgggc aactgcagcg tggccggctg gatcctgggc     240
aaccccgagt gcgagctgct gatcagcaag gagagctgga gctacatcgt ggagaagccc     300
aaccccgaga cggcacctg ctaccccggc cacttcgccg actacgagga gctgcgcgag      360
cagctgagca gcgtgagcag cttcgagcgc ttcgagatct cccccaagga gagcagctgg     420
cccaaccaca ccgtgaccgg cgtgagcgcc agctgcagcc acaacggcga gagcagcttc     480
taccgcaacc tgctgtggct gaccggcaag aacggcctgt accccaacct gagcaagagc     540
tacgccaaca acaaggagaa ggaggtgctg gtgctgtggg gcgtgcacca cccccccaac     600
atcggcgacc agaaggccct gtaccacacc gagaacgcct acgtgagcgt ggtgagcagc     660
cactacagcc gcaagttcac ccccgagatc gccaagcgcc ccaaggtgcg cgaccaggag     720
ggccgcatca actactactg gacctgctg gagcccggcg acaccatcat cttcgaggcc     780
aacggcaacc tgatcgcccc ccgctacgcc ttcgccctga gccgcggctt cggcagcggc     840
atcatcaaca gcaacgcccc catggacaag tgcgacgcca gtgccagac ccccagggc     900 gccatcaaca gcagcctgcc cttccagaac gtgcacccccg tgaccatcgg cgagtgcccc     960
aagtacgtgc gcagcgccaa gctgcgcatg gtgaccggcc tgcgcaacat ccccagcatc    1020
cagagccgcg gcctgttcgg cgccatcgcc ggcttcatcg agggcggctg gaccggcatg    1080
gtggacggct ggtacggcta ccaccaccag aacgagcagg gcagcggcta cgccgccgac    1140
cagaagagca cccagaacgc catcaacggc atcaccaaca aggtgaacag cgtgatcgag    1200
aagatgaaca cccagttcac cgccgtgggc aaggagttca acaagctgga gcgccgcatg    1260
gagaacctga acaagaaggt ggacgacggc ttcatcgaca tctggaccta caacgccgag    1320
ctgctggtgc tgctggagaa cgagcgcacc ctggacttcc acgacagcaa cgtgaagaac    1380
ctgtacgaga aggtgaagag ccagctgaag aacaacgcca aggagatcgg caacggctgc    1440
```

-continued

```
ttcgagttct accacaagtg caacgacgag tgcatggaga gcgtgaagaa cggcacctac    1500
gactacccca gtacagcga ggagagcaag ctgaaccgcg agaagatcga cggcgtgaag    1560
ctggagagca tgggcgtgta ccagatcctg gccatctaca gcaccgtggc cagcagcctg    1620
gtgctgctgg tgagcctggg cgccatcagc ttctggatgt gcagcaacgg cagcctgcag    1680
tgccgcatct gcatctaa                                                  1698
```

```
<210> SEQ ID NO 7
<211> LENGTH: 566
<212> TYPE: PRT
<213> ORGANISM: Influenza virus

<400> SEQUENCE: 7

Met Lys Thr Ile Ile Ala Leu Ser Tyr Ile Leu Cys Leu Val Phe Thr
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Gln Ser Ser Ser Thr
        50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Phe Pro Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
```

```
            325                 330                 335
Arg Asn Val Pro Glu Lys Gln Thr Arg Gly Ile Phe Gly Ala Ile Ala
        340                 345                 350
Gly Phe Ile Glu Asn Gly Trp Glu Gly Met Val Asp Gly Trp Tyr Gly
        355                 360                 365
Phe Arg His Gln Asn Ser Glu Gly Ile Gly Gln Ala Ala Asp Leu Lys
        370                 375                 380
Ser Thr Gln Ala Ala Ile Asp Gln Ile Asn Gly Lys Leu Asn Arg Leu
385                 390                 395                 400
Ile Gly Lys Thr Asn Glu Lys Phe His Gln Ile Glu Lys Glu Phe Ser
        405                 410                 415
Glu Val Glu Gly Arg Ile Gln Asp Leu Glu Lys Tyr Val Glu Asp Thr
        420                 425                 430
Lys Ile Asp Leu Trp Ser Tyr Asn Ala Glu Leu Leu Val Ala Leu Glu
        435                 440                 445
Asn Gln His Thr Ile Asp Leu Thr Asp Ser Glu Met Asn Lys Leu Phe
        450                 455                 460
Glu Lys Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
        485                 490                 495
Ile Arg Asn Gly Thr Tyr Asp His Asp Val Tyr Arg Asp Glu Ala Leu
        500                 505                 510
Asn Asn Arg Phe Gln Ile Lys Gly Val Glu Leu Lys Ser Gly Tyr Lys
        515                 520                 525
Asp Trp Ile Leu Trp Ile Ser Phe Ala Ile Ser Cys Phe Leu Leu Cys
        530                 535                 540
Val Ala Leu Leu Gly Phe Ile Met Trp Ala Cys Gln Lys Gly Asn Ile
545                 550                 555                 560
Arg Cys Asn Ile Cys Ile
                565

<210> SEQ ID NO 8
<211> LENGTH: 1701
<212> TYPE: DNA
<213> ORGANISM: Influenza virus

<400> SEQUENCE: 8
atgaagacca tcatcgccct gagctacatc ctgtgcctgg tgttcaccca gaagctgccc      60
ggcaacgaca acagcaccgc caccctgtgc ctgggccacc acgccgtgcc caacggcacc     120
atcgtgaaga ccatcaccaa cgaccagatc gaggtgacca acgccaccga gctggtgcag     180
agcagcagca ccggcgagat ctgcgacagc cccaccagat cctggacgg cgagaactgc     240 accctgatcg acgccctgct gggcgacccc cagtgcgacg gcttccagaa caagaagtgg     300
gacctgttcg tggagcgcag caaggcctac agcaactgct accccacga cgtgcccgac     360 tacgccagcc tgcgcagcct ggtggccagc agcggcaccc tggagttcaa caacgagagc     420
ttcaactgga ccggcgtgac ccagaacggc accagcagcg cctgcatccg ccgcagcaac     480
aacagcttct tcagccgcct gaactggctg acccacctga gttcaagta ccccgccctg     540 aacgtgacca tgcccaacaa cgagaagttc gacaagctgt acatctgggg cgtgcaccac     600
cccggcaccg acaacgacca gatcttcccc tacgcccagg ccagcggccg catcaccgtg     660
agcaccaagc gcagccagca gaccgtgatc cccaacatcg gcagccgccc ccgcgtgcgc     720
```

```
aacatcccca gccgcatcag catctactgg accatcgtga agcccggcga catcctgctg    780
atcaacagca ccggcaacct gatcgccccc cgcggctact tcaagatccg cagcggcaag    840
agcagcatca tgcgcagcga cgcccccatc ggcaagtgca acagcgagtg catcaccccc    900
aacggcagca tccccaacga caagcccttc cagaacgtga accgcatcac ctacggcgcc    960 tgccccgct acgtgaagca gaacaccctg aagctggcca ccggcatgcg caacgtgccc   1020
gagaagcaga cccgcggcat cttcggcgcc atcgccggct tcatcgagaa cggctgggag   1080
ggcatggtgg acggctggta cggcttccgc caccagaaca gcgagggcat cggccaggcc   1140
gccgacctga agagcaccca ggccgccatc gaccagatca cggcaagct gaaccgcctg    1200 atcggcaaga ccaacgagaa gttccaccag atcgagaagg agttcagcga ggtggagggc   1260
cgcatccagg acctggagaa gtacgtggag gacaccaaga tcgacctgtg gagctacaac   1320
gccgagctgc tggtggccct ggagaaccag cacaccatcg acctgaccga cagcgagatg   1380
aacaagctgt tcgagaagac caagaagcag ctgcgcgaga cgccgagga catgggcaac   1440 ggctgcttca agatctacca caagtgcgac aacgcctgca tcggcagcat ccgcaacggc   1500
acctacgacc acgacgtgta ccgcgacgag gccctgaaca accgcttcca gatcaagggc   1560
gtggagctga agagcggcta caaggactgg atcctgtgga tcagcttcgc catcagctgc   1620
ttcctgctgt gcgtggccct gctgggcttc atcatgtggg cctgccagaa gggcaacatc   1680
cgctgcaaca tctgcatcta a                                             1701
```

<210> SEQ ID NO 9
<211> LENGTH: 568
<212> TYPE: PRT
<213> ORGANISM: Influenza virus

<400> SEQUENCE: 9

```
Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Ile Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Arg Ser Ser Phe Phe
145                 150                 155                 160

Arg Asn Val Val Trp Leu Ile Lys Lys Asn Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
```

```
                195                 200                 205
Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Asn Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Gly Glu Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Arg Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 10
<211> LENGTH: 1707
<212> TYPE: DNA
<213> ORGANISM: Influenza virus

<400> SEQUENCE: 10
```

```
atggagaaga tcgtgctgct gctggccatc gtgagcctgg tgaagagcga ccagatctgc        60
atcggctacc acgccaacaa cagcaccgag caggtggaca ccatcatgga aaagaacgtg       120
accgtgaccc acgcccagga catcctggag aagacccaca cggcaagct gtgcgacctg        180
gacggcgtga agcccctgat cctgcgcgac tgcagcgtgg ccggctggct gctgggcaac       240
cccatgtgcg acgagttcct gaacgtgccc gagtggagct acatcgtgga aagatcaac       300
cccgccaacg acctgtgcta ccccggcaac ttcaacgact acgaggagct gaagcacctg       360
ctgagccgca tcaaccactt cgagaagatc cagatcatcc ccaagagcag ctggagcgac       420
cacgaggcca gcagcggcgt gagcagcgcc tgccccctac cagggccgcag cagcttcttc      480
cgcaacgtgg tgtggctgat caagaagaac aacgcctacc ccaccatcaa gcgcagctac      540
aacaacacca ccaggagga cctgctggtg ctgtggggca tccaccaccc caacgacgcc       600
gccgagcaga cccgcctgta ccagaacccc accacctaca tcagcgtggg caccagcacc      660
ctgaaccagc gcctggtgcc caagatcgcc acccgcagca aggtgaacgg ccagagcggc      720
cgcatggagt tcttctggac catcctgaag cccaacgacg ccatcaactt cgagagcaac      780
ggcaacttca tcgcccccga gaacgcctac aagatcgtga agaagggcga cagcaccatc      840
atgaagagcg agctggagta cggcaactgc aacaccaagt gccagacccc catcggcgcc      900
atcaacagca gcatgccctt ccacaacatc caccccctga ccatcggcga gtgccccaag      960
tacgtgaaga gcaaccgcct ggtgctggcc accggcctgc gcaacagccc cagggcgag      1020
cgccgccgca agaagcgcgg cctgttcggc gccatcgccg gcttcatcga gggcggctgg      1080
cagggcatgg tggacggctg gtacggctac caccacagca acgagcaggg cagcggctac      1140
gccgccgaca aggagagcac ccagaaggcc atcgacggcg tgaccaacaa ggtgaacagc     1200
atcatcgaca agatgaacac ccagttcgag gccgtgggcc gcgagttcaa caacctggag     1260
cgccgcatcg agaacctgaa caagaagatg gaggacggct tcctggacgt gtggacctac     1320
aacgccgagc tgctggtgct gatggagaac gagcgcaccc tggacttcca cgacagcaac     1380
gtgaagaacc tgtacgacaa ggtgcgcctg cagctgcgcg acaacgccaa ggagctgggc     1440
aacggctgct tcgagttcta ccaccgctgc gacaacgagt gcatggagag cgtgcgcaac     1500
ggcacctacg actacccca gtacagcgag gaggcccgcc tgaagcgcga ggagatcagc     1560
ggcgtgaagc tggagagcat cggcacctac cagatcctga gcatctacag caccgtggcc     1620
agcagcctgg ccctggccat catggtggcc ggcctgagcc tgtggatgtg cagcaacggc     1680
agcctgcagt gccgcatctg catctaa                                         1707
```

<210> SEQ ID NO 11
<211> LENGTH: 585
<212> TYPE: PRT
<213> ORGANISM: Influenza virus

<400> SEQUENCE: 11

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val

```
                65                  70                  75                  80
Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
        130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495
```

```
Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ala Ser Leu Asn Asp Asp Gly Leu
            530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585

<210> SEQ ID NO 12
<211> LENGTH: 1758
<212> TYPE: DNA
<213> ORGANISM: Influenza virus

<400> SEQUENCE: 12
atgaaggcca tcatcgtgct gctgatggtg gtgaccagca acgccgaccg catctgcacc      60
ggcatcacca gcagcaacag ccccccacgtg gtgaagaccg ccacccaggg cgaggtgaac     120
gtgaccggcg tgatccccct gaccaccacc cccaccaaga gccacttcgc caacctgaag     180
ggcaccgaga cccgcggcaa gctgtgcccc aagtgcctga actgcaccga cctggacgtg     240
gccctgggcc gccccaagtg caccggcaag atccccagcg cccgcgtgag catcctgcac     300
gaggtgcgcc ccgtgaccag cggctgcttc cccatcatgc acgaccgcac caagatccgc     360
cagctgccca acctgctgcg cggctacgag cacatccgcc tgagcaccca caacgtgatc     420
aacgccgaga acgcccccgg cggcccctac aagatcggca ccagcggcag ctgccccaac     480
atcaccaacg gcaacggctt cttcgccacc atggcctggg ccgtgcccaa gaacgacaag     540
aacaagaccg ccaccaaccc cctgaccatc gaggtgccct acatctgcac cgagggcgag     600
gaccagatca ccgtgtgggg cttccacagc gacaacgaga cccagatggc caagctgtac     660
ggcgacagca agccccagaa gttcaccagc agcgccaacg gcgtgaccac ccactacgtg     720
agccagatcg gcggcttccc caaccagacc gaggacggcg gcctgcccca gagcggccgc     780
atcgtggtgg actacatggt gcagaagagc ggcaagaccg gcaccatcac ctaccagcgc     840
ggcatcctgc tgccccagaa ggtgtggtgc gccagcggcc gcagcaaggt gatcaagggc     900
agcctgcccc tgatcggcga ggccgactgc ctgcacgaga gtacggcgg cctgaacaag     960 agcaagccct actacaccgg cgagcacgcc aaggccatcg gcaactgccc catctgggtg    1020
aagacccccc tgaagctggc caacggcacc aagtaccgcc ccccgccaa gctgctgaag    1080 gagcgcggct tcttcggcgc catcgccggc ttcctggagg cggctggga gggcatgatc    1140 gccggctggc acggctacac cagccacggc gcccacggcg tggccgtggc cgccgacctg    1200
aagagcaccc aggaggccat caacaagatc accaagaacc tgaacagcct gagcgagctg    1260
gaggtgaaga acctgcagcg cctgagcggc gccatggacg agctgcacaa cgagatcctg    1320
gagctggacg agaaggtgga cgacctgcgc gccgacacca tcagcagcca gatcgagctg    1380
gccgtgctgc tgagcaacga gggcatcatc aacagcgagg acgagcacct gctggccctg    1440
gagcgcaagc tgaagaagat cctgggcccc agcgccgtgg agatcggcaa cggctgcttc    1500
gagaccaagc acaagtgcaa ccagacctgc ctggaccgca tcgccgccgg caccttcgac    1560
```

| | |
|---|---|
| gccggcgagt tcagcctgcc caccttcgac agcctgaaca tcaccgccgc cagcctgaac | 1620 |
| gacgacggcc tggacaacca caccatcctg ctgtactaca gcaccgccgc cagcagcctg | 1680 |
| gccgtgaccc tgatgatcgc catcttcgtg gtgtacatgg tgagccgcga caacgtgagc | 1740 |
| tgcagcatct gcctgtaa | 1758 |

<210> SEQ ID NO 13
<211> LENGTH: 1701
<212> TYPE: DNA
<213> ORGANISM: Influenza virus

<400> SEQUENCE: 13

| | |
|---|---|
| atgaaagcaa aactactagt cctgttatgt gcatttacag ctacagatgc agacaccata | 60 |
| tgtataggct accatgcgaa caactcaacc gacactgttg acacagtact tgaaaagaac | 120 |
| gtgacagtga cacactctgt caacctactt gaggacagtc acaacggaaa actatgtcga | 180 |
| ctaaaaggaa tagccccact acaattgggt aattgcagca ttgccggatg gatcttagga | 240 |
| aacccagaat gcgaatcact gttttctaag aaatcatggt cctacattgc agaaacacca | 300 |
| aactccgaga atggaacatg ttacccaggg tatttcgccg actatgagga actgagggag | 360 |
| caattgagtt cagtatcatc attcgagaga ttcgaaatat tccccaaaga aagctcatgg | 420 |
| cccaaccaca ccgtaaccaa aggagtaacg gcatcatgct cccataaggg gagaagcagt | 480 |
| ttttacagaa atttgctatg gctgacgaag aagaatggcc cgtacccaaa tctgagcaag | 540 |
| tcctatgtga acaacaaaga gaaagaagtc cttgtactat ggggtgttca tcacccgtct | 600 |
| aacatagggg accaaagggc catctatcat acagaaaatg cttatgtctc tgtagtgtct | 660 |
| tcacattata caggagatt caccccagaa atagcaaaaa gacccaaagt aagagatcaa | 720 |
| gaaggaagaa ttaactacta ctggactctg ctggaacccg gggacacaat aatatttgag | 780 |
| gcaaatggaa atctaatagc gccatggtat gctttcgcac tgagtagagg ctttgggtca | 840 |
| ggaatcatca cctcaaacgc atcaatggat gaatgtgacg cgaagtgtca acaccccag | 900 |
| ggagctataa acagtagtct tccttttcag aatgtacacc cagtcacaat aggagagtgc | 960 |
| ccaaagtatg tcaggagtac aaaattaagg atggttacag gactaaggaa catcccatcc | 1020 |
| attcaatcca gaggtttgtt tggagccatt gccggtttca ttgaaggggg gtggactgga | 1080 |
| atgatagatg gatggtatgg ttatcatcat cagaatgaac aaggatctgg ctatgctgcg | 1140 |
| gatcaaaaaa gcacacaaaa tgccattaac gggattacaa caaggtgaa ttctgtaatc | 1200 |
| gagaaaatga acactcaatt cacagctgtg gcaaagaat tcaacaaatt agaaagaagg | 1260 |
| atggaaaact aaataaaaa agttgatgat ggatttctgg acatttggac atataatgca | 1320 |
| gaattgttgg ttctactgga aaatgaaagg actttggatt ttcatgactc aaatgtgaag | 1380 |
| aatctgtatg agaaagtaaa aagccaatta aagaataatg ccaaagaaat aggaaacggg | 1440 |
| tgttttgaat ctaccacaa gtgtaacaat gaatgcatgg aaagtgtgaa aaatggaact | 1500 |
| tatgactatc caaaatattc cgaggaatca aaattaaaca gggaaaaaat tgatggagtg | 1560 |
| aaattggaat caatgggagt ctatcagatt ctggcgatct actcaactgt cgccagttca | 1620 |
| ctggtgcttt tggtctccct gggggcaatc agcttctgga tgtgttctaa tgggtctttg | 1680 |
| cagtgtagaa tatgcatctg a | 1701 |

<210> SEQ ID NO 14
<211> LENGTH: 565
<212> TYPE: PRT
<213> ORGANISM: Influenza virus

```
<400> SEQUENCE: 14

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Arg Glu Ser Trp Ser Tyr Ile
                85                  90                  95

Val Glu Lys Pro Asn Pro Glu Asn Gly Thr Cys Tyr Pro Gly His Phe
                100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr
130                 135                 140

Thr Thr Gly Val Ser Ala Ser Cys Ser His Asn Gly Glu Ser Ser Phe
145                 150                 155                 160

Tyr Lys Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
            195                 200                 205

His Lys Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
            275                 280                 285

Asp Glu Cys Asp Ala Lys Cys Gln Thr Pro Gln Gly Ala Ile Asn Ser
290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
            370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
```

|  |  | 405 |  |  |  | 410 |  |  |  | 415 |  |
|---|---|---|---|---|---|---|---|---|---|---|---|
| Glu | Arg | Arg | Met | Glu | Asn | Leu | Asn | Lys | Lys | Val | Asp | Asp | Gly | Phe | Ile |
|  |  |  | 420 |  |  |  |  | 425 |  |  |  | 430 |  |  |  |

| Asp | Ile | Trp | Thr | Tyr | Asn | Ala | Glu | Leu | Leu | Val | Leu | Leu | Glu | Asn | Glu |
|---|---|---|---|---|---|---|---|---|---|---|---|---|---|---|---|
|  |  |  | 435 |  |  |  |  | 440 |  |  |  |  | 445 |  |  |

| Arg | Thr | Leu | Asp | Phe | His | Asp | Ser | Asn | Val | Lys | Asn | Leu | Tyr | Glu | Lys |
|---|---|---|---|---|---|---|---|---|---|---|---|---|---|---|---|
|  | 450 |  |  |  |  | 455 |  |  |  |  | 460 |  |  |  |  |

| Val | Lys | Ser | Gln | Leu | Lys | Asn | Asn | Ala | Lys | Glu | Ile | Gly | Asn | Gly | Cys |
|---|---|---|---|---|---|---|---|---|---|---|---|---|---|---|---|
| 465 |  |  |  |  | 470 |  |  |  |  | 475 |  |  |  |  | 480 |

| Phe | Glu | Phe | Tyr | His | Lys | Cys | Asn | Asp | Glu | Cys | Met | Glu | Ser | Val | Lys |
|---|---|---|---|---|---|---|---|---|---|---|---|---|---|---|---|
|  |  |  |  | 485 |  |  |  |  | 490 |  |  |  |  | 495 |  |

| Asn | Gly | Thr | Tyr | Asp | Tyr | Pro | Lys | Tyr | Ser | Glu | Glu | Ser | Lys | Leu | Asn |
|---|---|---|---|---|---|---|---|---|---|---|---|---|---|---|---|
|  |  |  | 500 |  |  |  |  | 505 |  |  |  | 510 |  |  |  |

| Arg | Glu | Lys | Ile | Asp | Gly | Val | Lys | Leu | Glu | Ser | Met | Gly | Val | Tyr | Gln |
|---|---|---|---|---|---|---|---|---|---|---|---|---|---|---|---|
|  | 515 |  |  |  |  | 520 |  |  |  |  | 525 |  |  |  |  |

| Ile | Leu | Ala | Ile | Tyr | Ser | Thr | Val | Ala | Ser | Ser | Leu | Val | Leu | Leu | Val |
|---|---|---|---|---|---|---|---|---|---|---|---|---|---|---|---|
| 530 |  |  |  |  | 535 |  |  |  |  | 540 |  |  |  |  |  |

| Ser | Leu | Gly | Ala | Ile | Ser | Phe | Trp | Met | Cys | Ser | Asn | Gly | Ser | Leu | Gln |
|---|---|---|---|---|---|---|---|---|---|---|---|---|---|---|---|
| 545 |  |  |  |  | 550 |  |  |  |  | 555 |  |  |  |  | 560 |

| Cys | Arg | Ile | Cys | Ile |
|---|---|---|---|---|
|  |  |  | 565 |  |

```
<210> SEQ ID NO 15
<211> LENGTH: 1698
<212> TYPE: DNA
<213> ORGANISM: Influenza virus

<400> SEQUENCE: 15
atgaaagcaa aactactggt cctgttatgt acatttacag ctacatatgc agacacaata      60
tgtataggct accatgccaa caactcaacc gacactgttg acacagtact tgagaagaat     120
gtgacagtga cacactctgt caacctactt gaggacagtc acaatggaaa actatgtcta     180
ctaaaaggaa tagccccact acaattgggt aattgcagcg ttgccggatg gatcttagga     240
aacccagaat gcgaattact gatttccaag gaatcatggt cctacattgt agaaacacca     300
aatcctgaga atggaacatg ttacccaggg tatttcgccg actatgagga actgagggag     360
caattgagtt cagtatcttc atttgagaga ttcgaaatat cccccaaaga agctcatggc     420
cccaaccaca ccgtaaccgg agtatcagca tcatgctccc ataatgggaa aagcagtttt     480
tacagaaatt tgctatggct gacggggaag aatggttttgt acccaaacct gagcaagtcc     540
tatgtaaaca caaagagaa agaagtcctt gtactatggg gtgttcatca cccgcctaac     600
atagggaacc aaagggccct ctatcataca gaaaatgctt atgtctctgt agtgtcttca     660
cattatagca gaagattcac cccagaaata gccaaaagac ccaaagtaag agatcaggaa     720
ggaagaatca actactactg gactctgctg gaacctgggg atacaataat atttgaggca     780
aatggaaatc taatagcgcc atggtatgct tttgcactga gtagaggctt tggatcagga     840
atcatcacct caaatgcacc aatggatgaa tgtgatgcga agtgtcaaac acctcaggga     900
gctataaaca gcagtcttcc tttccagaat gtacacccag tcacaatagg agagtgtcca     960
aagtatgtca ggagtgcaaa attaaggatg gttacaggac taaggaacat cccatccatt    1020
caatccagag gtttgtttgg agccattgcc ggtttcattg aaggggggtg gactggaatg    1080
gtagatgggt ggtatggtta tcatcatcag aatgagcaag gatctggcta tgctgcagat    1140
caaaaaagta cacaaaatgc cattaacggg attacaaaca aggtgaattc tgtaattgag    1200
```

```
aaaatgaaca ctcaattcac agctgtgggc aaagaattca acaaattgga agaaggatg   1260 gaaaacttaa ataaaaaagt tgatgatggg tttctagaca tttggacata taatgcagaa   1320
ttgttggttc tactggaaaa tgaaaggact ttggatttcc atgactccaa tgtgaagaat   1380
ctgtatgaga agtaaaaaag ccaattaaag aataatgcca agaaataggg aaacgggtgt   1440
tttgaattct atcacaagtg taacaatgaa tgcatggaga gtgtgaaaaa tggaacttat   1500
gactatccaa atattccga agaatcaaag ttaaacaggg agaaaattga tggagtgaaa   1560
ttggaatcaa tgggagtcta tcagattctg gcgatctact caactgtcgc cagttccctg   1620
gttcttttgg tctccctggg ggcaatcagc ttctggatgt gttccaatgg gtctttgcag   1680
tgtagaatat gcatctga                                                1698
```

<210> SEQ ID NO 16
<211> LENGTH: 565
<212> TYPE: PRT
<213> ORGANISM: Influenza sequence

<400> SEQUENCE: 16

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Thr His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
```

-continued

```
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 17
<211> LENGTH: 1698
<212> TYPE: DNA
<213> ORGANISM: Influenza sequence

<400> SEQUENCE: 17
atgaaagtaa aactactggt cctgttatgc acatttacag ctacatatgc agacacaata      60
tgtataggct accatgccaa caactcaacc gacactgttg acacagtact tgagaagaat     120
gtgacagtga cacactctgt caacctgctt gaggacagtc acaatggaaa attatgtcta     180
ttaaaaggaa tagccccact acaattgggt aattgcagcg ttgccggatg gatcttagga     240
aacccagaat gcgaattact gatttccagg gaatcatggt cctacattgt agaaaaacca     300
aatcctgaga atggaacatg ttacccaggg catttcgccg actatgagga actgagggag     360
caattgagtt cagtatcttc atttgagaga ttcgaaatat tccccaaaga aagctcatgg     420
cccaaccaca ccacaaccgg agtatcagca tcatgctccc ataatgggga aagcagtttt     480
```

```
tacaaaaatt tgctatggct gacggggaag aatggtttgt acccaaacct gagcaagtcc    540
tatgcaaaca caaagagaa agaagtcctt gtactatggg gtgttcatca cccgcctaac    600
ataggtgacc aaagggctct ctatcataaa gaaaatgctt atgtctctgt agtgtcttca    660
cattatagca gaaaattcac cccagaaata gccaaaagac ccaaagtaag agatcaagaa    720
ggaagaatca actactactg gactctactt gaacccgggg atacaataat atttgaggca    780
aatgaaaatc taatagcgcc aagatatgct ttcgcactga gtagaggctt tggatcagga    840
atcatcaact caaatgcacc aatggatgaa tgtgatgcga agtgccaaac acctcaggga    900
gctataaaca gcagtcttcc tttccagaat gtacaccctg tcacaatagg agagtgtcca    960
aagtatgtca ggagtgcaaa attaaggatg ttacaggac taaggaacat cccatccatt    1020
caatccagag gtttgtttgg agccattgcc ggtttcattg aaggggggtg gactggaatg   1080
gtagatggtt ggtatggtta tcatcatcag aatgagcaag gatctggcta tgctgcagat    1140
caaaaaagca cacaaaatgc cattaatggg attacaaaca aggtgaattc tgtaattgag    1200
aaaatgaaca ctcaattcac agctgtgggc aaagaattca caaaattgga agaaggatg    1260 gaaaacttaa ataaaaaagt tgatgatggg tttatagca tttggacata taatgcagaa    1320 tgttggttc tactggaaaa tgaaaggact ttggatttcc atgactccaa tgtgaagaat    1380
ctgtatgaga agtaaaaaag ccaattaaag aataatgcca agaaatagg aaatgggtgt    1440 tttgaattct atcataagtg taacgatgaa tgcatggaga gtgtaaaaaa tggaacttat    1500
gactatccaa atattccga gaatcaaag ttaaacaggg agaaaattga tggagtgaaa    1560
ttggaatcaa tgggagtcta tcagattctg gcgatctact caacagtcgc cagttctctg    1620
gttcttttgg tctccctggg ggcaatcagc ttctggatgt gttccaatgg gtctttgcag    1680
tgtagaatat gcatctga                                                 1698
```

<210> SEQ ID NO 18
<211> LENGTH: 565
<212> TYPE: PRT
<213> ORGANISM: Influenza virus

<400> SEQUENCE: 18

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Arg Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Thr Thr Gly Val Ser Ala Ser Cys Ser His Asn Gly Glu Ser Ser Phe
```

-continued

```
145                 150                 155                 160
Tyr Lys Asn Leu Leu Trp Leu Thr Gly Lys Asn Gly Leu Tyr Pro Asn
                165                 170                 175
Leu Ser Lys Ser Tyr Ala Asn Asn Lys Glu Lys Glu Val Leu Val Leu
                180                 185                 190
Trp Gly Val His His Pro Pro Asn Ile Gly Asp Gln Arg Ala Leu Tyr
                195                 200                 205
His Lys Glu Asn Ala Tyr Val Ser Val Val Ser Ser His Tyr Ser Arg
210                 215                 220
Lys Phe Thr Pro Glu Ile Ala Lys Arg Pro Lys Val Arg Asp Gln Glu
225                 230                 235                 240
Gly Arg Ile Asn Tyr Tyr Trp Thr Leu Leu Glu Pro Gly Asp Thr Ile
                245                 250                 255
Ile Phe Glu Ala Asn Gly Asn Leu Ile Ala Pro Arg Tyr Ala Phe Ala
                260                 265                 270
Leu Ser Arg Gly Phe Gly Ser Gly Ile Ile Asn Ser Asn Ala Pro Met
                275                 280                 285
Asp Glu Cys Asp Ala Lys Cys Gln Thr Pro Gln Gly Ala Ile Asn Ser
                290                 295                 300
Ser Leu Pro Phe Gln Asn Val His Pro Val Thr Ile Gly Glu Cys Pro
305                 310                 315                 320
Lys Tyr Val Arg Ser Ala Lys Leu Arg Met Val Thr Gly Leu Arg Asn
                325                 330                 335
Ile Pro Ser Ile Gln Ser Arg Gly Leu Phe Gly Ala Ile Ala Gly Phe
                340                 345                 350
Ile Glu Gly Gly Trp Thr Gly Met Val Asp Gly Trp Tyr Gly Tyr His
                355                 360                 365
His Gln Asn Glu Gln Gly Ser Gly Tyr Ala Ala Asp Gln Lys Ser Thr
                370                 375                 380
Gln Asn Ala Ile Asn Gly Ile Thr Asn Lys Val Asn Ser Val Ile Glu
385                 390                 395                 400
Lys Met Asn Thr Gln Phe Thr Ala Val Gly Lys Glu Phe Asn Lys Leu
                405                 410                 415
Glu Arg Arg Met Glu Asn Leu Asn Lys Lys Val Asp Asp Gly Phe Ile
                420                 425                 430
Asp Ile Trp Thr Tyr Asn Ala Glu Leu Leu Val Leu Leu Glu Asn Glu
                435                 440                 445
Arg Thr Leu Asp Phe His Asp Ser Asn Val Lys Asn Leu Tyr Glu Lys
450                 455                 460
Val Lys Ser Gln Leu Lys Asn Asn Ala Lys Glu Ile Gly Asn Gly Cys
465                 470                 475                 480
Phe Glu Phe Tyr His Lys Cys Asn Asp Glu Cys Met Glu Ser Val Lys
                485                 490                 495
Asn Gly Thr Tyr Asp Tyr Pro Lys Tyr Ser Glu Glu Ser Lys Leu Asn
                500                 505                 510
Arg Glu Lys Ile Asp Gly Val Lys Leu Glu Ser Met Gly Val Tyr Gln
                515                 520                 525
Ile Leu Ala Ile Tyr Ser Thr Val Ala Ser Ser Leu Val Leu Leu Val
                530                 535                 540
Ser Leu Gly Ala Ile Ser Phe Trp Met Cys Ser Asn Gly Ser Leu Gln
545                 550                 555                 560
Cys Arg Ile Cys Ile
                565
```

<210> SEQ ID NO 19
<211> LENGTH: 1698
<212> TYPE: DNA
<213> ORGANISM: Influenza virus

<400> SEQUENCE: 19

| | | | | | |
|---|---|---|---|---|---|
| atgaaagtaa | aactactggt | cctgttatgc | acatttacag | ctacatatgc | agacacaata | 60 |
| tgtataggct | accatgctaa | caactcgacc | gacactgttg | acacagtact | tgaaaagaat | 120 |
| gtgacagtga | cacactctgt | caacctgctt | gagaacagtc | acaatggaaa | actatgtcta | 180 |
| ttaaaaggaa | tagccccact | acaattgggt | aattgcagcg | ttgccgggtg | gatcttagga | 240 |
| aacccagaat | gcgaattact | gatttccaag | gagtcatggt | cctacattgt | agaaaaacca | 300 |
| aatcctgaga | atggaacatg | ttacccaggg | catttcgctg | actatgagga | actgagggag | 360 |
| caattgagtt | cagtatcttc | atttgagagg | ttcgaaatat | ccccaaaga | aagctcatgg | 420 |
| cccaaccaca | ccgtaaccgg | agtgtcagca | tcatgctccc | ataatgggga | aagcagtttt | 480 |
| tacagaaatt | tgctatggct | gacggggaag | aatggtttgt | acccaaacct | gagcaagtcc | 540 |
| tatgcaaaca | caaagaaaaa | agaagtcctt | gtactatggg | gtgttcatca | cccgccaaac | 600 |
| ataggtgacc | aaaaggccct | ctatcataca | gaaaatgctt | atgtctctgt | agtgtcttca | 660 |
| cattatagca | gaaaattcac | cccagaaata | gccaaaagac | ccaaagtaag | agatcaagaa | 720 |
| ggaagaatca | attactactg | gactctgctt | gaacccgggg | atacaataat | atttgaggca | 780 |
| aatggaaatc | taatagcgcc | aagatatgct | ttcgcactga | gtagaggctt | tggatcagga | 840 |
| atcatcaact | caaatgcacc | aatggataaa | tgtgatgcga | agtgccaaac | acctcaggga | 900 |
| gctataaaca | gcagtcttcc | tttccagaac | gtacacccag | tcacaatagg | agagtgtcca | 960 |
| aagtatgtca | ggagtgcaaa | attaaggatg | gttacaggac | taaggaacat | cccatccatt | 1020 |
| caatccagag | gtttgtttgg | agccattgcc | ggtttcattg | aagggggtg | gactggaatg | 1080 |
| gtagatggtt | ggtatggtta | tcatcatcag | aatgagcaag | gatctggcta | tgctgcagat | 1140 |
| caaaaaagca | cacaaaatgc | cattaatggg | attacaaaca | aggtgaattc | tgtaattgag | 1200 |
| aaaatgaaca | ctcaattcac | agcagtgggc | aaagaattca | acaaattgga | agaaggatg | 1260 |
| gaaaacttga | ataaaaaagt | tgatgatggg | tttatagaca | tttggacata | taatgcagaa | 1320 |
| ctgttggttc | tactggaaaa | tgaaaggact | ttggatttcc | atgactccaa | tgtgaagaat | 1380 |
| ctgtatgaga | aagtaaaaag | ccagttaaag | aataatgcta | agaaatagg | aaatgggtgt | 1440 |
| tttgaattct | atcacaagtg | taacgatgaa | tgcatggaga | gtgtaaagaa | tggaacttat | 1500 |
| gactatccaa | atattccga | agaatcaaag | ttaaacaggg | agaaaattga | tggagtgaaa | 1560 |
| ttggaatcaa | tgggagtcta | tcagattctg | gcgatctact | caacagtcgc | cagttctctg | 1620 |
| gttcttttgg | tctccctggg | ggcaatcagc | ttctggatgt | gttccaatgg | gtctttacag | 1680 |
| tgtagaatat | gcatctaa | | | | | 1698 |

<210> SEQ ID NO 20
<211> LENGTH: 565
<212> TYPE: PRT
<213> ORGANISM: Influenza Virus

<400> SEQUENCE: 20

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr

```
            20                  25                  30
Val Asp Thr Val Leu Glu Lys Asn Val Thr Val Thr His Ser Val Asn
             35                  40                  45

Leu Leu Glu Asn Ser His Asn Gly Lys Leu Cys Leu Leu Lys Gly Ile
 50                  55                  60

Ala Pro Leu Gln Leu Gly Asn Cys Ser Val Ala Gly Trp Ile Leu Gly
 65                  70                  75                  80

Asn Pro Glu Cys Glu Leu Leu Ile Ser Lys Glu Ser Trp Ser Tyr Ile
                 85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr
            130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Lys Ala Leu Tyr
            195                 200                 205

His Thr Glu Asn Ala Tyr Val Ser Val Ser Ser His Tyr Ser Arg
            210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
            275                 280                 285

Asp Lys Cys Asp Ala Lys Cys Gln Thr Pro Gln Gly Ala Ile Asn Ser
            290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
            370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
            435                 440                 445
```

```
Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
                500                 505                 510

Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 21
<211> LENGTH: 1701
<212> TYPE: DNA
<213> ORGANISM: Influenza Virus

<400> SEQUENCE: 21
atgaagacta tcattgcttt gagctacatt ttatgtctgg ttttcgctca aaaacttccc      60
ggaaatgaca cagcacggc  aacgctgtgc ctgggacacc atgcagtgcc aaacggaacg     120
ctagtgaaaa caatcacgaa tgaccaaatt gaagtgacta atgctactga gctggttcag     180
agttcctcaa caggtagaat atgcgacagt cctcaccaaa tccttgatgg agaaaactgc     240
acactgatag atgctctatt gggagaccca cattgtgatg gcttccaaaa taaggaatgg     300 gaccttttg  ttgaacgcag caaagcctac agcaactgtt acccttatga tgtgccggat     360
tatgcctccc ttaggtcact agttgcctca tccggcaccc tggagtttaa caatgaaagc     420
ttcaattgga ctggagtcgc tcagaatgga caagctctt  cttgcaaaag gagatctatt     480
aaaagtttct ttagtagatt gaattggttg caccaattaa aatacagata tccagcactg     540
aacgtgacta tgccaaacaa tgacaaattt gacaaattgt acatttgggg ggttcaccac     600
ccgagtacgg acagtgacca aaccagccta tacccaag   catcagggag agtcacagtc     660
tctaccaaaa gaagccaaca aactgtaatc ccgaatatcg atccagaccc tgggtaagg    720 ggtatctcca gcagaataag catctattgg acaatagtaa aaccgggaga catactttg    780 attaacagca cagggaatct aattgctcct cgggggttact tcaaaatacg aagtgggaaa     840
agctcaataa tgaggtcaga tgcacccatt ggcaaatgca attctgaatg catcactcca     900
aatggaagca ttcccaatga caaaccatt  caaaatgtaa acaggatcac atatgggggcc    960 tgtcccagat atgttaagca aaacactctg aaattggcaa cagggatgcg gaatgtacca    1020
gagaaacaaa ctagaggcat attcggcgca atcgcgggtt tcatagaaaa tggttgggag    1080
ggaatgatgg acgttggta  cggttttcagg catcaaaatt ctgagggcac aggacaagca    1140
gcagatctta aaagcactca agcagcaatc aaccaaatca acgggaaact gaataggtta    1200
atcgagaaaa cgaacgagaa attccatcaa attgaaaaag aattctcaga agtagaaggg    1260
agaattcagg acctcgagaa atatgttgag gacactaaaa tagatctctg gtcgtacaac    1320
gcggagcttc ttgttgccct ggagaaccaa catacaattg atctaactga ctcagaaatg    1380
```

-continued

```
aacaaactgt tgaaagaac aaggaagcaa ctgagagaaa atgctgagga tatgggcaat    1440
ggttgtttca aaatatacca caaatgtgac aatgcctgca tagggtcaat cagaaatgga    1500
acttatgacc atgatgtata cagagacgaa gcattaaaca accggttcca gatcaaaggt    1560
gttgagctga agtcaggata caaagattgg atcctatgga tttcctttgc catatcatgt    1620
tttttgcttt gtgttgtttt gctggggttc attatgtggg cctgccaaaa aggcaacatt    1680
aggtgcaaca tttgcatttg a                                              1701
```

```
<210> SEQ ID NO 22
<211> LENGTH: 566
<212> TYPE: PRT
<213> ORGANISM: Influenza Virus

<400> SEQUENCE: 22
```

| Met | Lys | Thr | Ile | Ile | Ala | Leu | Ser | Tyr | Ile | Leu | Cys | Leu | Val | Phe | Ala |
|---|---|---|---|---|---|---|---|---|---|---|---|---|---|---|---|
| 1 | | | | 5 | | | | | 10 | | | | | 15 | |

| Gln | Lys | Leu | Pro | Gly | Asn | Asp | Asn | Ser | Thr | Ala | Thr | Leu | Cys | Leu | Gly |
|---|---|---|---|---|---|---|---|---|---|---|---|---|---|---|---|
| | | | 20 | | | | | 25 | | | | | 30 | | |

| His | His | Ala | Val | Pro | Asn | Gly | Thr | Leu | Val | Lys | Thr | Ile | Thr | Asn | Asp |
|---|---|---|---|---|---|---|---|---|---|---|---|---|---|---|---|
| | | 35 | | | | | 40 | | | | | 45 | | | |

| Gln | Ile | Glu | Val | Thr | Asn | Ala | Thr | Glu | Leu | Val | Gln | Ser | Ser | Ser | Thr |
|---|---|---|---|---|---|---|---|---|---|---|---|---|---|---|---|
| | 50 | | | | | 55 | | | | | 60 | | | | |

| Gly | Arg | Ile | Cys | Asp | Ser | Pro | His | Gln | Ile | Leu | Asp | Gly | Glu | Asn | Cys |
|---|---|---|---|---|---|---|---|---|---|---|---|---|---|---|---|
| 65 | | | | | 70 | | | | | 75 | | | | | 80 |

| Thr | Leu | Ile | Asp | Ala | Leu | Leu | Gly | Asp | Pro | His | Cys | Asp | Gly | Phe | Gln |
|---|---|---|---|---|---|---|---|---|---|---|---|---|---|---|---|
| | | | | 85 | | | | | 90 | | | | | 95 | |

| Asn | Lys | Glu | Trp | Asp | Leu | Phe | Val | Glu | Arg | Ser | Lys | Ala | Tyr | Ser | Asn |
|---|---|---|---|---|---|---|---|---|---|---|---|---|---|---|---|
| | | | 100 | | | | | 105 | | | | | 110 | | |

| Cys | Tyr | Pro | Tyr | Asp | Val | Pro | Asp | Tyr | Ala | Ser | Leu | Arg | Ser | Leu | Val |
|---|---|---|---|---|---|---|---|---|---|---|---|---|---|---|---|
| | | 115 | | | | | 120 | | | | | 125 | | | |

| Ala | Ser | Ser | Gly | Thr | Leu | Glu | Phe | Asn | Asn | Glu | Ser | Phe | Asn | Trp | Thr |
|---|---|---|---|---|---|---|---|---|---|---|---|---|---|---|---|
| | 130 | | | | | 135 | | | | | 140 | | | | |

| Gly | Val | Ala | Gln | Asn | Gly | Thr | Ser | Ser | Cys | Lys | Arg | Arg | Ser | Ile |
|---|---|---|---|---|---|---|---|---|---|---|---|---|---|---|
| 145 | | | | | 150 | | | | | 155 | | | | | 160 |

| Lys | Ser | Phe | Phe | Ser | Arg | Leu | Asn | Trp | Leu | His | Gln | Leu | Lys | Tyr | Arg |
|---|---|---|---|---|---|---|---|---|---|---|---|---|---|---|---|
| | | | | 165 | | | | | 170 | | | | | 175 | |

| Tyr | Pro | Ala | Leu | Asn | Val | Thr | Met | Pro | Asn | Asn | Asp | Lys | Phe | Asp | Lys |
|---|---|---|---|---|---|---|---|---|---|---|---|---|---|---|---|
| | | | 180 | | | | | 185 | | | | | 190 | | |

| Leu | Tyr | Ile | Trp | Gly | Val | His | His | Pro | Ser | Thr | Asp | Ser | Asp | Gln | Thr |
|---|---|---|---|---|---|---|---|---|---|---|---|---|---|---|---|
| | | 195 | | | | | 200 | | | | | 205 | | | |

| Ser | Leu | Tyr | Thr | Gln | Ala | Ser | Gly | Arg | Val | Thr | Val | Ser | Thr | Lys | Arg |
|---|---|---|---|---|---|---|---|---|---|---|---|---|---|---|---|
| | 210 | | | | | 215 | | | | | 220 | | | | |

| Ser | Gln | Gln | Thr | Val | Ile | Pro | Asn | Ile | Gly | Ser | Arg | Pro | Trp | Val | Arg |
|---|---|---|---|---|---|---|---|---|---|---|---|---|---|---|---|
| 225 | | | | | 230 | | | | | 235 | | | | | 240 |

| Gly | Ile | Ser | Ser | Arg | Ile | Ser | Ile | Tyr | Trp | Thr | Ile | Val | Lys | Pro | Gly |
|---|---|---|---|---|---|---|---|---|---|---|---|---|---|---|---|
| | | | | 245 | | | | | 250 | | | | | 255 | |

| Asp | Ile | Leu | Leu | Ile | Asn | Ser | Thr | Gly | Asn | Leu | Ile | Ala | Pro | Arg | Gly |
|---|---|---|---|---|---|---|---|---|---|---|---|---|---|---|---|
| | | | 260 | | | | | 265 | | | | | 270 | | |

| Tyr | Phe | Lys | Ile | Arg | Ser | Gly | Lys | Ser | Ser | Ile | Met | Arg | Ser | Asp | Ala |
|---|---|---|---|---|---|---|---|---|---|---|---|---|---|---|---|
| | | 275 | | | | | 280 | | | | | 285 | | | |

| Pro | Ile | Gly | Lys | Cys | Asn | Ser | Glu | Cys | Ile | Thr | Pro | Asn | Gly | Ser | Ile |
|---|---|---|---|---|---|---|---|---|---|---|---|---|---|---|---|
| | 290 | | | | | 295 | | | | | 300 | | | | |

| Pro | Asn | Asp | Lys | Pro | Phe | Gln | Asn | Val | Asn | Arg | Ile | Thr | Tyr | Gly | Ala |
|---|---|---|---|---|---|---|---|---|---|---|---|---|---|---|---|
| 305 | | | | | 310 | | | | | 315 | | | | | 320 |

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Met Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 23
<211> LENGTH: 1699
<212> TYPE: DNA
<213> ORGANISM: Influenza Virus

<400> SEQUENCE: 23
atgaagacta tcattgcttt gagctacatt ctatgtctgg ttttcgctca aaaacttccc    60
ggaaatgaca cagcacggc aacgctgtgc cttgggcacc atgcagtacc aaacggaacg    120
atagtgaaaa caatcacgaa tgaccaaatt gaagttacta atgctactga gctggttcag    180
agttcttcaa caggtggaat atgcgacagt cctcatcaga tccttgatgg agaaaactgc    240
acactaatag atgctctatt gggagaccct cagtgtgatg cttccaaaa taagaaatgg    300 gacctttttg ttgaacgcag caaagcctac agcaactgtt acccttatga tgtgccggat    360
tatgcctccc ttaggtcact agttgcctca tccggcacac tggagtttaa caatgaaagc    420
ttcaattgga ctggagtcac tcaaaatgga acaagctctg cttgcaaaag agatctcaat    480
aacagtttct ttagtaaatt gaattggttg acccatttaa aattcaaata cccagcattg    540
aacgtgacta tgccaaacaa tgaaaaattt gacaaattgt acatttgggg ggttcaccac    600
ccgggtacga acaatgacca aatcagccta tatgctcaag catcaggaag aatcacagtc    660

-continued

```
tctaccaaaa gaagccaaca aactgtaatc ccgaatatcg gatctagacc cagggtaagg    720
gatatcccca gtagaataag catctattgg acaatagtaa aaccgggaga catactttg     780
attaacagca cagggaatct aattgctcct cggggttact tcaaaatacg aagtgggaaa    840
agctcaataa tgagatcaga tgcacccatt ggcaaatgca attctgaatg catcactcca    900
aatggaagca ttcccaatga caaccatttt caaaatgtaa acaggatcac atatggggcc    960
tgtcccagat atgttaagca aaacactctg aaattggcaa cagggatgcg aaatgtacca   1020
gagaaacaaa ctagaggcat atttggcgca atcgcgggtt tcatagaaaa tggttgggag   1080
ggaatggtgg atggttggta cggtttcagg catcaaaatt ctgagggaat aggacaagca   1140
gcagatctca aaagcactca agcagcaatc aaccaaatca tgggaagct gaataggttg    1200
atcgggaaaa ccaacgagaa attccatcag attgaaaaag aattctcaga agtagaaggg   1260
agaattcagg acctcgagaa atatgttgag gacactaaaa tagatctctg gtcatacaac   1320
gcggagcttc ttgttgccct ggagaaccaa catacaattg acctaactga ctcagaaatg   1380
aacaaactgt ttgaaagaac aaagaagcaa ctgagggaaa atgctgagga tatgggcaat   1440
ggttgtttca aaatatacca caaatgtgac aatgcctgca tagggtcaat cagaaatgga   1500
acttatgacc atgatgtata cagagatgaa gcattaaaca accggttcca gatcaaaggt   1560
gttgagctga agtcaggata caaagattgg atcctatgga tttcctttgc catatcatgt   1620
tttttgcttt gtgttgcttt gttggggttc atcatgtggg cctgccaaaa aggcaacatt   1680
aggtgcaaca tttgcattt                                                1699
```

<210> SEQ ID NO 24
<211> LENGTH: 566
<212> TYPE: PRT
<213> ORGANISM: Influenza Virus

<400> SEQUENCE: 24

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Lys Arg Arg Ser Asn
145                 150                 155                 160

Asn Ser Phe Phe Ser Lys Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190
```

Leu Tyr Ile Trp Gly Val His His Pro Gly Thr Asn Asn Asp Gln Ile
            195                 200                 205

Ser Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asp Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 25
<211> LENGTH: 1701
<212> TYPE: DNA
<213> ORGANISM: Influenza virus

<400> SEQUENCE: 25

```
atgaagacta tcattgcttt gagctacatt ctatgtctgg ttttcgctca aaaacttccc        60
ggaaatgaca acagcacggc aacgctgtgc cttgggcacc atgcagtacc aaacggaacg       120
atagtgaaaa caatcacgaa tgaccaaatt gaagttacta atgctactga gctggttcag       180
agttcctcaa caggtggaat atgcgacagt cctcatcaga tccttgatgg agaaaactgc       240
acactaatag atgctctatt gggagaccct cagtgtgatg cttccaaaa taagaaatgg       300
gacctttttg ttgaacgcag caaagcctac agcaactgtt acccttatga tgtgccggat       360
tatgcctccc ttaggtcact agttgcctca tccggcacac tggagtttaa cgatgaaagc       420
ttcaattgga ctggagtcac tcaaaatgga acaagctctt cttgcaaaag agatctaat       480
aacagtttct ttagtagatt gaattggttg acccaattaa aattcaaata cccagcattg       540
aacgtgacta tgccaaacaa tgaaaaattt gacaaattgt catttgggg ggttcaccac       600
ccggttacgg acaatgacca atcttcctg tatgctcaag catcaggaag aatcacagtc       660
tctaccaaaa gaagccaaca aactgtaatc ccgaatatcg atctagacc cagaataagg       720
aatatcccca gcagaataag catctattgg acaatagtaa accgggaga catacttttg       780
attaacagca cagggaatct aattgctcct aggggttact tcaaaatacg aagtgggaaa       840
agctcaataa tgagatcaga tgcacccatt ggcaaatgca attctgaatg catcactcca       900
aatggaagca ttcccaatga caaaccattt caaaatgtaa acaggatcac atatgggcc       960
tgtcccagat atgttaagca aaacactctg aaattggcaa cagggatgcg aaatgtacca      1020
gagaaacaaa ctagaggcat atttggcgca atcgcgggtt tcatagaaaa tggttgggag      1080
ggaatggtgg atggttggta cggtttcagg catcaaaatt ctgagggaat aggacaagca      1140
gcagatctca aaagcactca agcagcaatc aatcaaatca tgggaagct gaataggttg      1200
atcgggaaaa ccaacgagaa attccatcag attgaaaag aattctcaga agtagaaggg      1260
agaattcagg acctcgagaa atatgttgag gacactaaaa tagatctctg gtcatacaac      1320
gcggagcttc ttgttgccct ggagaaccaa catacaattg atctaactga ctcagaaatg      1380
aacaaactgt ttgaaagaac aaagaagcaa ctgagggaaa atgctgagga tatgggcaat      1440
ggttgtttca aaatatacca caaatgtgac aatgcctgca taggatcaat cagaaatgga      1500
acttatgacc atgatgtata cagagatgaa gcattaaaca accggttcca gatcaaaggc      1560
gttgagctga agtcaggata caaagattgg atcctatgga tttcctttgc catatcatgt      1620
ttttgctttt gtgttgcttt gttggggttc atcatgtggg cctgccaaa aggcaacatt      1680
aggtgcaaca tttgcatttg a                                                  1701
```

<210> SEQ ID NO 26
<211> LENGTH: 566
<212> TYPE: PRT
<213> ORGANISM: Influenza virus

<400> SEQUENCE: 26

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60
```

```
Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
            85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Asn Asp Glu Ser Phe Asn Trp Thr
130                 135                 140

Gly Val Thr Gln Asn Gly Thr Ser Ser Ser Cys Lys Arg Arg Ser Asn
145                 150                 155                 160

Asn Ser Phe Phe Ser Arg Leu Asn Trp Leu Thr His Leu Lys Phe Lys
            165                 170                 175

Tyr Pro Ala Leu Asn Val Thr Met Pro Asn Asn Glu Lys Phe Asp Lys
            180                 185                 190

Leu Tyr Ile Trp Gly Val His His Pro Val Thr Asp Asn Asp Gln Ile
            195                 200                 205

Phe Leu Tyr Ala Gln Ala Ser Gly Arg Ile Thr Val Ser Thr Lys Arg
210                 215                 220

Ser Gln Gln Thr Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
            245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
            275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
            325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
            355                 360                 365

Phe Arg His Gln Asn Ser Glu Gly Ile Gly Gln Ala Ala Asp Leu Lys
            370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
            405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
            450                 455                 460

Glu Arg Thr Lys Lys Gln Leu Arg Glu Asn Ala Glu Asp Met Gly Asn
465                 470                 475                 480
```

```
Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 27
<211> LENGTH: 1701
<212> TYPE: DNA
<213> ORGANISM: Influenza Virus

<400> SEQUENCE: 27
atgaagacta tcattgcttt gagctacatt ctatgtctgg ttttcactca aaaacttccc      60
ggaaatgaca acagcacggc aacgctgtgc cttgggcacc atgcagtacc aaacggaacg     120
atagtgaaaa caatcacgaa tgaccaaatt gaagttacta atgctactga gctggttcag     180
agttcctcaa caggtgaaat atgcgacagt cctcatcaga tccttgatgg agaaaactgc     240
acactaatag atgctctatt gggagaccct cagtgtgatg gcttccaaaa taagaaatgg     300
gacctttttg ttgaacgcag caaagcctac agcaactgtt acccttatga tgtgccggat     360
tatgcctccc ttaggtcact agttgcctca tccggcacac tggagtttaa caatgaaagc     420
ttcaattgga ctggagtcac tcaaaacgga acaagctctg cttgcataag agatctaat      480
aacagtttct ttagtagatt gaattggttg acccacttaa aattcaaata cccagcattg     540
aacgtgacta tgccaaacaa tgaaaaattt gacaaattgt acatttgggg ggttcaccac     600
ccgggtacgg acaatgacca aatcttcccg tatgctcaag catcaggaag aatcacagtc     660
tctaccaaaa gaagccaaca aactgtaatc ccgaatatcg gatctagacc cagagtaagg     720
aatatcccca gcagaataag catctattgg acaatagtaa accgggagag catacttttg     780
attaacagca cagggaatct aattgctcct agggggttact tcaaaatacg aagtgggaaa     840
agctcaataa tgagatcaga tgcacccatt ggcaaatgca attctgaatg catcactcca     900
aacggaagca ttcccaatga caaaccattc caaaatgtaa acaggatcac atacgggggcc    960
tgtcccagat atgttaagca aaacactctg aaattggcaa cagggatgcg aaatgtacca    1020
gagaaacaaa ctagaggcat atttggcgca atcgcgggtt tcatagaaaa tggttgggag    1080
ggaatggtgg atggttggta cggtttcagg catcaaaatt ctgagggaat aggacaagca    1140
gcagatctca aaagcactca agcagcaatc gatcaaatca tgggaagct gaataggttg    1200
atcgggaaaa ccaacgagaa attccatcag attgaaaaag aattctcaga agtcgaaggg    1260
agaattcagg accttgagaa atatgttgag gacaccaaaa tagatctctg gtcatacaac    1320
gcggagcttc ttgttgccct ggagaaccaa catacaattg atctaactga ctcagaaatg    1380
aacaaactgt ttgaaaaaac aaagaagcaa ctgagggaaa atgctgagga tatgggcaat    1440
ggttgtttca aaatatacca caatgtgac aatgcctgca taggatcaat cagaaatgga    1500
acttatgacc acgatgtata cagagatgaa gcattaaaca accggttcca gatcaagggc    1560
gttgagctga agtcaggata caaagattgg atcctatgga tttcctttgc catatcatgt    1620
```
tttttgcttt gtgttgcttt gttggggttc atcatgtggg cctgccaaaa aggcaacatt    1680
aggtgcaaca tttgcatttg a                                              1701

<210> SEQ ID NO 28
<211> LENGTH: 566
<212> TYPE: PRT
<213> ORGANISM: Influenza virus

<400> SEQUENCE: 28

Met Lys Thr Ile Ile Ala Leu Ser Tyr Ile Leu Cys Leu Val Phe Thr
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Phe Pro Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

```
Gly Phe Ile Glu Asn Gly Trp Glu Gly Met Val Asp Gly Trp Tyr Gly
                355                 360                 365
Phe Arg His Gln Asn Ser Glu Gly Ile Gly Gln Ala Ala Asp Leu Lys
            370                 375                 380
Ser Thr Gln Ala Ala Ile Asp Gln Ile Asn Gly Lys Leu Asn Arg Leu
385                 390                 395                 400
Ile Gly Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
435                 440                 445
Asn Gln His Thr Ile Asp Leu Thr Asp Ser Glu Met Asn Lys Leu Phe
            450                 455                 460
Glu Lys Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asp Val Tyr Arg Asp Glu Ala Leu
            500                 505                 510
Asn Asn Arg Phe Gln Ile Lys Gly Val Glu Leu Lys Ser Gly Tyr Lys
            515                 520                 525
Asp Trp Ile Leu Trp Ile Ser Phe Ala Ile Ser Cys Phe Leu Leu Cys
            530                 535                 540
Val Ala Leu Leu Gly Phe Ile Met Trp Ala Cys Gln Lys Gly Asn Ile
545                 550                 555                 560
Arg Cys Asn Ile Cys Ile
                565

<210> SEQ ID NO 29
<211> LENGTH: 1707
<212> TYPE: DNA
<213> ORGANISM: Influenza virus

<400> SEQUENCE: 29
atggagaaaa tagtgcttct ttttgcaata gtcagtcttg ttaaaagtga tcagatttgc    60
attggttacc atgcaaacaa ctcgacagag caggttgaca caataatgga aaagaacgtt   120
actgttacac atgcccaaga catactggaa agaaacaca acgggaagct ctgcgatcta   180
gatggagtga agcctctaat tttgagagat tgtagcgtag ctggatggct cctcggaaac   240
ccaatgtgtg acgaattcat caatgtgccg gaatggtctt acatagtgga aaggccaat   300 ccagtcaatg acctctgtta cccaggggat tcaatgact atgaagaatt gaaacaccta   360
ttgagcagaa taaccatttt gagaaaatt cagatcatcc ccaaaagttc ttggtccagt   420
catgaagcct cattagggg gagctcagca tgtccatacc agggaaagtc ctcctttttc   480
agaaatgtgg tatggcttat caaaaagaac agtacatacc aacaataaa gaggagctac   540 aataatacca accaagaaga tctttttggta ctgtggggga ttcaccatcc taatgatgcg   600
gcagagcaga caaagctcta tcaaaaccca accacctata tttccgttgg gacatcaaca   660
ctaaaccaga gattggtacc aagaatagct actagatcca agtaaacgg gcaaagtgga   720 aggatggagt tcttctggac aatttttaaag ccgaatgatg caatcaactt cgagagtaat   780
ggaaattcca ttgctccaga atatgcatac aaaattgtca gaaaggggga ctcaacaatt   840
atgaaaagtg aattggaata tggtaactgc aacaccaagt gtcaaactcc aatgggggcg   900
```

```
ataaactcta gcatgccatt ccacaatata caccctctca ccattgggga atgccccaaa    960
tatgtgaaat caaacagatt agtccttgcg actgggctca gaaatagccc tcaaagagag   1020
agaagaagaa aaaagagagg attatttgga gctatagcag gttttataga gggaggatgg   1080
cagggaatgg tagatggttg gtatgggtac caccatagca atgagcaggg gagtgggtac   1140
gctgcagaca aagaatccac tcaaaaggca atagatggag tcaccaataa ggtcaactcg   1200
atcattgaca aaatgaacac tcagtttgag gccgttggaa gggaatttaa caacttagaa   1260
aggagaatag agaatttaaa caagaagatg gaagacgggt tcctagatgt ctggacttat   1320
aatgctgaac ttctggttct catggaaaat gagagaactc tagactttca tgactcaaat   1380
gtcaagaacc tttacgacaa ggtccgacta cagcttaggg ataatgcaaa ggagctgggt   1440
aacggttgtt tcgagttcta tcataaatgt gataatgaat gtatggaaag tgtaagaaat   1500
ggaacgtatg actacccgca gtattcagaa gaagcgagac taaaaagaga ggaaataagt   1560
ggagtaaaat tggaatcaat aggaatttac caaatactgt caatttattc tacagtggcg   1620
agttccctag cactggcaat catggtagct ggtctatcct tatggatgtg ctccaatgga   1680
tcgttacaat gcagaatttg catttaa                                       1707

<210> SEQ ID NO 30
<211> LENGTH: 568
<212> TYPE: PRT
<213> ORGANISM: Influenza virus

<400> SEQUENCE: 30

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220
```

```
Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Ile Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 31
<211> LENGTH: 1707
<212> TYPE: DNA
<213> ORGANISM: Influenza virus

<400> SEQUENCE: 31
atggagaaaa tagtgcttct tcttgcaata gtcagtcttg ttaaaagtga tcagatttgc    60
attggttacc atgcaaacaa ctcgacagag caggttgaca caataatgga aaagaacgtc   120
actgttacac acgcccaaga catactggaa aagacacaca acgggaagct ctgcgatcta   180
```

```
gatggagtga agcctctaat tttaagagat tgtagtgtag ctggatggct cctcgggaac    240
ccaatgtgtg acgaattcct caatgtgccg gaatggtctt acatagtgga aagatcaat     300 ccagccaatg acctctgtta cccagggaat ttcaacgact atgaagaact gaaacaccta    360
ttgagcagaa taaccatttt tgagaaaatt cagataatcc ccaaaagttc ttggtcagat    420
catgaagcct catcaggggt gagctcagca tgtccatacc agggaaggtc ctcctttttt    480
agaaatgtgg tatggcttat caaaaagaac aatgcatacc caacaataaa gagaagttac    540
aacaatacca accaagaaga tcttttggta ctgtggggga ttcaccatcc aaatgatgcg    600
gcagagcaga caaggctcta tcaaaaccca accacctata tttccgttgg gacatcaaca    660
ctaaatcaga gattggtacc aaaaatagct actagatcca aggtaaacgg caaagtggaa    720
aggatggagt tcttttggac aattttaaaa ccgaatgatg caataaactt gagagtaat     780 ggaaatttca ttgctccaga aaatgcatac aaaattgtca agaaggggga ctcaacaatt    840
atgaaaagtg aattggaata tggtaactgc aacaccaagt gtcaaactcc aatagggcg     900 ataaactcta gtatgccatt ccacaacatc caccctctca ccatcgggga atgccccaaa    960
tatgtgaaat caaacagatt agtccttgcg actgggctca gaaatagccc tcaaggagag   1020
agaagaagaa aaagagagg actatttgga gctatagcag gttttataga gggaggatgg    1080
cagggaatgg tagatggttg gtatgggtac caccatagca acgagcaggg gagtgggtac    1140
gctgcagaca agaatccact caaaaggca atagatggag tcaccaataa ggtcaactcg    1200
atcattgaca aatgaacac tcagtttgag gctgttggaa gggaatttaa taacttagaa    1260
aggagaatag aaaatttaaa caagaagatg aagacggat tcctagatgt ctggacttat    1320
aatgctgaac ttctggttct catggaaaat gagagaactc tagactttca tgactcaaat    1380
gttaagaacc tttacgacaa ggtccgacta cagcttaggg ataatgcaaa ggagcttggt    1440
aacggttgtt tcgagttcta tcacagatgt gataatgaat gtatggaaag tgtaagaaac    1500
ggaacgtatg actacccgca gtattcagaa gaagcaagat taaaaagaga ggaaataagt    1560
ggagtaaaat tggaatcaat aggaacttac caaatactgt caatttattc aacagtggcg    1620
agctccctag cactggcaat catggtggct ggtctatctt tatggatgtg ctccaatgga    1680
tcgttacaat gcagaatttg catttaa                                        1707
```

<210> SEQ ID NO 32
<211> LENGTH: 568
<212> TYPE: PRT
<213> ORGANISM: Influenza Virus

<400> SEQUENCE: 32

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95
```

-continued

```
Glu Lys Ile Asn Pro Ala Asn Asp Leu Cys Tyr Pro Gly Asn Phe Asn
                100                 105                 110
Asp Tyr Glu Glu Leu Lys His Leu Leu Ser Arg Ile Asn His Phe Glu
            115                 120                 125
Lys Ile Gln Ile Ile Pro Lys Ser Ser Trp Ser Asp His Glu Ala Ser
        130                 135                 140
Ser Gly Val Ser Ser Ala Cys Pro Tyr Gln Gly Arg Ser Ser Phe Phe
145                 150                 155                 160
Arg Asn Val Val Trp Leu Ile Lys Lys Asn Asn Ala Tyr Pro Thr Ile
                165                 170                 175
Lys Arg Ser Tyr Asn Asn Thr Asn Gln Glu Asp Leu Leu Val Leu Trp
            180                 185                 190
Gly Ile His His Pro Asn Asp Ala Ala Glu Gln Thr Arg Leu Tyr Gln
        195                 200                 205
Asn Pro Thr Thr Tyr Ile Ser Val Gly Thr Ser Thr Leu Asn Gln Arg
    210                 215                 220
Leu Val Pro Lys Ile Ala Thr Arg Ser Lys Val Asn Gly Gln Ser Gly
225                 230                 235                 240
Arg Met Glu Phe Phe Trp Thr Ile Leu Lys Pro Asn Asp Ala Ile Asn
                245                 250                 255
Phe Glu Ser Asn Gly Asn Phe Ile Ala Pro Glu Asn Ala Tyr Lys Ile
            260                 265                 270
Val Lys Lys Gly Asp Ser Thr Ile Met Lys Ser Glu Leu Glu Tyr Gly
        275                 280                 285
Asn Cys Asn Thr Lys Cys Gln Thr Pro Ile Gly Ala Ile Asn Ser Ser
    290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Ser
                325                 330                 335
Pro Gln Gly Glu Arg Arg Arg Lys Lys Arg Gly Leu Phe Gly Ala Ile
            340                 345                 350
Ala Gly Phe Ile Glu Gly Gly Trp Gln Gly Met Val Asp Gly Trp Tyr
        355                 360                 365
Gly Tyr His His Ser Asn Glu Gln Gly Ser Gly Tyr Ala Ala Asp Lys
    370                 375                 380
Glu Ser Thr Gln Lys Ala Ile Asp Gly Val Thr Asn Lys Val Asn Ser
385                 390                 395                 400
Ile Ile Asp Lys Met Asn Thr Gln Phe Glu Ala Val Gly Arg Glu Phe
                405                 410                 415
Asn Asn Leu Glu Arg Arg Ile Glu Asn Leu Asn Lys Lys Met Glu Asp
            420                 425                 430
Gly Phe Leu Asp Val Trp Thr Tyr Asn Ala Glu Leu Leu Val Leu Met
        435                 440                 445
Glu Asn Glu Arg Thr Leu Asp Phe His Asp Ser Asn Val Lys Asn Leu
    450                 455                 460
Tyr Asp Lys Val Arg Leu Gln Leu Arg Asp Asn Ala Lys Glu Leu Gly
465                 470                 475                 480
Asn Gly Cys Phe Glu Phe Tyr His Arg Cys Asp Asn Glu Cys Met Glu
                485                 490                 495
Ser Val Arg Asn Gly Thr Tyr Asp Tyr Pro Gln Tyr Ser Glu Glu Ala
            500                 505                 510
Arg Leu Lys Arg Glu Glu Ile Ser Gly Val Lys Leu Glu Ser Ile Gly
```

```
              515                 520                 525
Thr Tyr Gln Ile Leu Ser Ile Tyr Ser Thr Val Ala Ser Ser Leu Ala
            530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 33
<211> LENGTH: 1758
<212> TYPE: DNA
<213> ORGANISM: Influenza Virus

<400> SEQUENCE: 33
atgaaggcaa taattgtact actcatggta gtaacatcca atgcagatcg aatctgcact      60
ggaataacat cgtcaaactc accacatgtc gtcaaaactg ctactcaagg ggaggtcaat     120
gtgactggtg taataccact gacaacaaca cccaccaaat ctcattttgc aaatctcaaa     180
ggaacagaaa ccaggggaa  actatgccca aaatgcctca actgcacaga tctggacgta     240
gccttgggca gaccaaaatg cacggggaaa ataccctcgg caagagtttc aatactccat     300
gaagtcagac ctgttacatc tgggtgcttt cctataatgc acgacagaac aaaaattaga     360
cagctgccta accttctccg aggatacgaa catatcaggt tatcaaccca taacgttatc     420
aatgcagaaa atgcaccagg aggaccctac aaaattggaa cctcagggtc ttgccctaac     480
attaccaatg gaaacggatt tttcgcaaca atggcttggg ccgtcccaaa aaacgacaaa     540
aacaaaacag caacaaatcc attaacaata gaagtaccat acatttgtac agaaggagaa     600
gaccaaatta ccgtttgggg gttccactct gacaacgaga cccaaatggc aaagctctat     660
ggggactcaa agcccagaa  gttcacctca tctgccaacg gagtgaccac acattacgtt     720
tcacagattg gtggcttccc aaatcaaaca gaagacggag gactaccaca agtggtaga      780 attgttgttg attacatggt gcaaaatct  gggaaaacag gaacaattac ctatcaaagg     840
ggtattttat gcctcaaaa  ggtgtggtgc gcaagtggca ggagcaaggt aataaaagga     900
tccttgcctt taattggaga agcagattgc ctccacgaaa atacggtgg  attaaacaaa     960 agcaagcctt actacacagg gaacatgca  aaggccatag aaattgccc  aatatgggtg    1020 aaaacaccct tgaagctggc caatggaacc aaatatagac tcctgcaaa  actattaaag    1080 gaaaggggtt tcttcggagc tattgctggt ttcttagaag aggatgggaa ggaatgatt     1140 gcaggttggc acgatacac  atcccatggg gcacatggag tagcggtggc agcagacctt    1200
aagagcactc aagaggccat aaacaagata caaaaaatc  tcaactcttt gagtgagctg    1260
gaagtaaaga atcttcaaag actaagcggt gccatggatg aactccacaa cgaaatacta    1320
gaactagatg agaaagtgga tgatctcaga gctgatacaa taagctcaca aatagaactc    1380
gcagtcctgc tttccaatga aggaataata aacagtgaag atgaacatct cttggcgctt    1440
gaaagaaagc tgaagaaaat gctgggcccc tctgctgtag atagggaa  tggatgcttt     1500 gaaaccaaac acaagtgcaa ccagacctgt ctcgacagaa tagctgctgg tacctttgat    1560
gcaggagaat tttctctccc cacctttgat tcactgaata ttactgctgc atctttaaat    1620
gacgatggat tggataatca tactatactg ctttactact caactgctgc ctccagtttg    1680
gctgtaacac tgatgatagc tatctttgtt gtttatatgg tctccagaga caatgtttct    1740
tgctccatct gtctataa                                                  1758
```

<210> SEQ ID NO 34
<211> LENGTH: 585
<212> TYPE: PRT
<213> ORGANISM: Influenza Virus

<400> SEQUENCE: 34

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
370                 375                 380

```
Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
            405                 410                 415

Leu Ser Glu Leu Glu Val Lys Asn Leu Gln Arg Leu Ser Gly Ala Met
        420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
            485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ala Ser Leu Asn Asp Asp Gly Leu
        530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
            565                 570                 575

Asp Asn Val Ser Cys Ser Ile Cys Leu
            580                 585

<210> SEQ ID NO 35
<211> LENGTH: 1755
<212> TYPE: DNA
<213> ORGANISM: Influenza Virus

<400> SEQUENCE: 35
atgaaggcaa taattgtact actcatggta gtaacatcca atgcagatcg aatctgcact      60
ggaataacat cttcaaactc acctcatgtg gtcaaaacag ccactcaagg ggaggtcaat     120
gtgactggtg tgataccact aacaacaaca ccaacaaaat cttattttgc aaatctcaaa     180
ggaacaagga ccagagggaa actatgccca gactgtctca actgcacaga tctggatgtg     240
gctttgggca gaccaatgtg tgtggggacc acaccttcgg cgaaagcttc aatactccac     300
gaagtcaaac tgttacatc cgggtgcttt cctataatgc acgacagaac aaaaatcagg     360
caactaccca tcttctcag aggatatgaa aatatcaggc tatcaaccca aaacgtcatc     420
gatgcggaaa aggcaccagg aggaccctac agacttggaa cctcaggatc ttgccctaac     480
gctaccagta gagcggatt tttcgcaaca atggcttggg ctgtcccaaa ggacaacaac     540
aaaaatgcaa cgaacccact aacagtagaa gtaccataca tttgtacaga aggggaagac     600
caaatcactg tttgggggtt ccattcagat gacaaaaccc aaatgaagaa cctctatgga     660
gactcaaatc ctcaaaagtt cacctcatct gctaatggag taaccacaca ctatgtttct     720
cagattggca gcttcccaga tcaaacagaa gacggaggac taccacaaag cggcaggatt     780
gttgttgatt acatgatgca aaacctgggg aaaacaggaa caattgtcta ccaaagaggt     840
gttttgttgc ctcaaaaggt gtggtgcgcg agtggcagga caaagtaat aaaagggtcc     900 ttgcctttaa ttggtgaagc agattgcctt catgaaaaat acggtggatt aaacaaaagc     960
```

```
aagccttact acacaggaga acatgcaaaa gccataggaa attgcccaat atgggtgaaa    1020
acacctttga agcttgccaa tggaaccaaa tatagacctc ctgcaaaact attaaaggaa    1080
aggggtttct tcggagctat tgctggtttc ctagaaggag gatgggaagg aatgattgca    1140
ggctggcacg gatacacatc tcacggagca catggagtgg cagtggcggc ggaccttaag    1200
agtacgcaag aagctataaa caagataaca aaaaatctca attctttgag tgagctagaa    1260
gtaaagaatc ttcaaagact aagtggtgcc atggatgaac tccacaacga atactcgag     1320 ctggatgaga aagtggatga tctcagagct gacactataa gctcgcaaat agaacttgca    1380
gtcttgcttt ccaacgaagg aataataaac agtgaagatg agcatctatt ggcacttgag    1440
agaaaactaa agaaaatgct gggtccctct gctgtagaga taggaaatgg atgcttcgaa    1500
accaaacaca agtgcaacca gacctgctta gacaggatag ctgctggcac ctttaatgca    1560
ggagaatttt ctctccccac ttttgattca ctgaacatta ctgctgcatc tttaaatgat    1620
gatggattgg ataaccatac tatactgctc tattactcaa ctgctgcttc tagtttggct    1680
gtaacattga tgctagctat ttttattgtt tatatggtct ccagagacaa cgtttcatgc    1740
tccatctgtc tataa                                                    1755
```

<210> SEQ ID NO 36
<211> LENGTH: 584
<212> TYPE: PRT
<213> ORGANISM: Influenza Virus

<400> SEQUENCE: 36

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Lys Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Lys Asp Asn Asn Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asp Lys Thr Gln Met Lys Asn Leu Tyr Gly Asp Ser Asn Pro
    210                 215                 220
```

Gln Lys Phe Thr Ser Ser Ala Asn Gly Val Thr His Tyr Val Ser
225                 230                 235                 240

Gln Ile Gly Ser Phe Pro Asp Gln Thr Glu Asp Gly Gly Leu Pro Gln
            245                 250                 255

Ser Gly Arg Ile Val Val Asp Tyr Met Met Gln Lys Pro Gly Lys Thr
        260                 265                 270

Gly Thr Ile Val Tyr Gln Arg Gly Val Leu Leu Pro Gln Lys Val Trp
    275                 280                 285

Cys Ala Ser Gly Arg Ser Lys Val Ile Lys Gly Ser Leu Pro Leu Ile
290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Glu Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Leu Ala Ile Phe Ile Val Tyr Met Val Ser Arg Asp
                565                 570                 575

Asn Val Ser Cys Ser Ile Cys Leu
            580

<210> SEQ ID NO 37
<211> LENGTH: 1698
<212> TYPE: DNA
<213> ORGANISM: Influenza virus

<400> SEQUENCE: 37
atgaaggcaa tactagtagt tctgctatat acatttgcaa ccgcaaatgc agacacatta        60

| | | |
|---|---|---|
| tgtataggtt atcatgcgaa caattcaaca gacactgtag acatagtact agaaaagaat | 120 | |
| gtaacagtaa cacactctgt taaccttcta gaagacaagc ataacgggaa actatgcaaa | 180 | |
| ctaagagggg tagccccatt gcatttgggt aaatgtaaca ttgctggctg atcctggga | 240 | |
| aatccagagt gtgaatcact ctccacagca agctcatggt cctacattgt ggaaacatct | 300 | |
| agttcagaca atggaacgtg ttacccagga gatttcatcg attatgagga gctaagagag | 360 | |
| caattgagct cagtgtcatc atttgaatgg tttgagatat tccccaagac aagttcatgg | 420 | |
| cccaatcatg actcgaacaa aggtgtaacg gcagcatgtc ttcatgctgg agcaaaaagc | 480 | |
| ttctacaaaa atttaatatg gctagttaaa aaaggaaatt cacccccaaa gctcagcaaa | 540 | |
| tcctacatta atgataaagg gaaagaagtc ctcgtgctat ggggcattca ccatccatct | 600 | |
| actagtgctg accaacaaag tctctatcag aatgcagatg catatgtttt tgtggggaca | 660 | |
| tcaagataca gcaagaagtt caagccggaa atagcaataa gacccaaagt gagggatcaa | 720 | |
| gaagggagaa tgaactatta ctggacacta gtagagccgg gagacaaaat aacattcgaa | 780 | |
| gcaactggaa atcagtggt accgagatat gcattcgcaa tggaaagaaa tgctggatct | 840 | |
| ggtattatca tttcagatac accagtccac gattgcaata caacttgtca gacacccaag | 900 | |
| ggtgctataa acaccagcct cccatttcag aatatacatc cgatcacaat ggaaaaatgt | 960 | |
| ccaaaatatg tagaaagcac aaaattgaga ctggccacag gattgaggaa tgtcccgtct | 1020 | |
| attcaatcta gaggcctatt tggggccatt gccggtttca ttgaagggggg gtggacaggg | 1080 | |
| atggtagatg gatggtacgg ttatcaccat caaaatgagc aggggtcagg atatgcagcc | 1140 | |
| gacctgaaga gcacacagaa tgccattgac gagattacta caaagtaaa ttctgttatt | 1200 | |
| gaaaagatga atacacaatt cacagcagta ggtaaagagt caaccaccct ggaaaaaaga | 1260 | |
| atagagaatt taaataaaaa aattgatgat ggtttcctgg acatttggac ttacaatgcc | 1320 | |
| gaactgttgg ttctattgga aaatgaaaga actttggact atcacgattc aaatgtgaag | 1380 | |
| aacttatatg aaaaggtaag aagccagtta aaaaacaatg ccaaggaaat tggaaacggc | 1440 | |
| tgctttgaat tttaccacaa atgcgataac acgtgcatgg aaagtgtcaa aaatgggact | 1500 | |
| tatgactacc caaatactc agaggaagca aaattaaaca gagaagaaat agatggggta | 1560 | |
| aagctggaat caacaaggat ttaccagatt ttggcgatct attcaactgt cgccagttca | 1620 | |
| ttggtactgg tagtctccct gggggcaatc agtttctgga tgtgctctaa tgggtctcta | 1680 | |
| cagtgtagaa tatgtatt | 1698 | |

<210> SEQ ID NO 38
<211> LENGTH: 566
<212> TYPE: PRT
<213> ORGANISM: Influenza Virus

<400> SEQUENCE: 38

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Ile Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80
```

```
Asn Pro Glu Cys Glu Ser Leu Ser Thr Ala Ser Ser Trp Ser Tyr Ile
                 85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Trp Phe Glu Ile Phe Pro Lys Thr Ser Ser Trp Pro Asn His Asp
            130                 135                 140

Ser Asn Lys Gly Val Thr Ala Ala Cys Leu His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Thr Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
            275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Glu Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Ile Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
```

-continued

```
                500                 505                 510
Asn Arg Glu Glu Ile Asp Gly Val Lys Leu Glu Ser Thr Arg Ile Tyr
            515                 520                 525

Gln Ile Leu Ala Ile Tyr Ser Thr Val Ala Ser Ser Leu Val Leu Val
        530                 535                 540

Val Ser Leu Gly Ala Ile Ser Phe Trp Met Cys Ser Asn Gly Ser Leu
545                 550                 555                 560

Gln Cys Arg Ile Cys Ile
                565
```